(12) United States Patent
Tykocinski et al.

(10) Patent No.: US 7,435,585 B2
(45) Date of Patent: Oct. 14, 2008

(54) AUTO-STIMULATING CELLS AND METHODS FOR MAKING AND USING THE SAME

(75) Inventors: Mark L. Tykocinski, Philadelphia, PA (US); Guoxing Zheng, Philadelphia, PA (US)

(73) Assignee: University of Pennsylvania, Philadelphia, PA (US)

( * ) Notice: Subject to any disclaimer, the term of this patent is extended or adjusted under 35 U.S.C. 154(b) by 747 days.

(21) Appl. No.: 10/205,524

(22) Filed: Jul. 25, 2002

(65) Prior Publication Data

US 2003/0206917 A1 Nov. 6, 2003

Related U.S. Application Data

(60) Continuation-in-part of application No. 09/957,056, filed on Sep. 20, 2001, which is a division of application No. 09/476,828, filed on Jan. 3, 2000, now Pat. No. 6,316,256.

(60) Provisional application No. 60/398,050, filed on Jul. 22, 2002.

(51) Int. Cl.
  *C12N 5/00* (2006.01)
  *C12N 5/02* (2006.01)
  *C12N 5/06* (2006.01)
  *C12N 5/16* (2006.01)
(52) U.S. Cl. .................. 435/325; 435/326; 435/328; 435/329
(58) Field of Classification Search .................. 435/325, 435/326, 328, 329
See application file for complete search history.

(56) References Cited

U.S. PATENT DOCUMENTS

| | | | |
|---|---|---|---|
| 5,242,687 | A | 9/1993 | Tykocinski et al. |
| 5,601,828 | A | 2/1997 | Tykocinski et al. |
| 5,623,056 | A | 4/1997 | Tykocinski et al. |
| 5,698,679 | A | 12/1997 | Nemazee |
| 5,817,789 | A | 10/1998 | Heartlein et al. |
| 6,027,921 | A | 2/2000 | Heartlein et al. |
| 6,316,256 | B1 | 11/2001 | Tykocinski et al. |

OTHER PUBLICATIONS

Brunschwig et al., J. Immunolo., 155:5498 (1995).
McHugh et al., Proc. Natl. Acad. Sci. USA, 92:8059 (1995).
McHugh et al., Cancer Res., 59:2433 (1999).
Kim and Peacock, J. Immunol. Methods, 158:57 (1993).
Phillips et al., "CD94 and a Novel Associated Protein (94AP) Form a NK Cell Receptor Involved in the Recognition of HLA-A, HLA-B, and HLA-C Allotypes," Immunity, vol. 5:163-172 (Aug. 1996).
Darling et al., "In Vitro immune modulation by antibodies coupled to tumor cells", Gene Therapy, 4(12):1350-60 (Dec. 1997).
Londo et al., "Lateral Diffusion of Antigen Receptors Artificially Incorporated Onto B Lymphocytes," The Journal of Immunology, vol. 137, 1924-1931, No. 6 (Sep. 15, 1986).
Peacock et al., "Biologic Activity of Antigen Receptors Artificially Incorporated Onto B Lymphocytes", The Journal of Immunology, vol. 137, 1916-1923, No. 6 (Sep. 15, 1986).
Colsky et al., "Surrogate Receptor-Mediated Cellular Cytotoxicity", The Journal of Immunology, vol. 140, 2515-2519, No. 8, (Apr. 15, 1988).
Colsky and Peacock, "Palmitate-derivatized antibodies can function as surrogate receptors for mediating specific cell-cell interactions", Journal of Immunological Methods, vol. 124, 179-187 (1989).
Matzinger, "A simple assay for DNA fragmentation and cell death", Journal of Immunological Methods, vol. 145, 185-192 (1991).
Gura, Systems for Identifying New Drugs are Often Faulty, Science, Nov. 7, 1997, pp. 1041-1042, vol. 278.
Jain, Barriers to Drug Delivery in Solid Tumors, Scientific American, Jul. 1994, 271(1) pp. 58-65.

*Primary Examiner*—Alana M. Harris
(74) *Attorney, Agent, or Firm*—Meyer, Unkovic & Scott LLP; Debra Z. Anderson

(57) ABSTRACT

Methods for transferring one or more proteins to a cell are disclosed. The protein or proteins to be transferred are in the form of a fusion protein, and contain at least one domain encoding for a protein or peptide having trans signaling and/or adhesion function. The fusion protein is transferred to a cell by binding to a lipidated protein, which has been incorporated into the cell membrane. In an additional aspect of the invention, methods of making fusion proteins having cis signaling capabilities, as well as the ability to bind with receptors on the cell's own surface, are provided. Fusion proteins incorporating GPI or a homing element, and a costimulator or inhibitor domain can also be directly transferred to the cell surface. Methods for using cells which have undergone protein transfer according to the present methods are also disclosed. This includes use in a cancer vaccine, use for treatment of cancer or autoimmune disease, and use in determining costimulator threshold levels.

23 Claims, 21 Drawing Sheets

EL-4

Human T cells

| Mixture | Components | | Mode of costimulation |
|---|---|---|---|
| | MT-treated | Non-treated | |
| A |  CoS |  | trans |
| B |  |  CoS | trans + cis |
| C |  |  | none |

US 7,435,585 B2

AUTO-STIMULATING CELLS AND METHODS FOR MAKING AND USING THE SAME

CROSS-REFERENCE TO RELATED APPLICATION

This application claims priority under 35 USC § 119(e) to Provisional Application Ser. No. 60/398,050, filed Jul. 22, 2002, and is a continuation-in-part of application Ser. No. 09/957,056. filed Sep. 20, 2001, which is a divisional application of 09/476,828, filed Jan. 3, 2000, now U.S. Pat. No. 6,316,256, expressly incorporated herein by reference.

This work was supported in part by Grants R01 CA-74958 and R01 AI-31044 from the National Institutes of Health.

FIELD OF THE INVENTION

The present invention relates to novel methods for transferring one or more proteins to a cell. In addition to other applications, the methodology is useful in the treatment of cancer and autoimmune diseases, and for determining costimulator activation thresholds and cooperative interactions among costimulators. The invention further relates to cells painted with extrinsic proteins that are capable of triggering receptors on the surfaces of the same cells. Methods of making such auto-stimulating cells and using them as therapeutic agents are also disclosed.

BACKGROUND INFORMATION

T-cells, including cytotoxic T-lymphocytes, are a critical component of effective human immune responses to tumors, viral infections and other infectious diseases. T-cells destroy neoplastic or virally infected cells through recognition of antigenic peptides presented by MHC class I molecules on the surfaces of target cells. Activation of T-cells is dependent upon coordinate signaling through antigen receptors and costimulator receptors on T-cell surfaces. Antigen presentation, in the absence of simultaneous costimulation, can paradoxically lead to clonal anergy (See, Gimmi et al., Proc. Natl. Acad. Sci. USA, 90:6586 (1993)).

Antigen-presenting cells (APC), such as dendritic cells, are geared towards potent T cell activation, by virtue of their surface MHC and costimulator molecules that can trigger their cognate receptors on specific T cells and thereby provide both critical signals to them (See, Watts et al., Curr. Opin. Immunol., 11:286 (1999); Freedman et al., Cell. Immunol., 137:429 (1991)). Thus, according to the prevalent APC-centric view of T cell regulation, T cell activation is generally viewed as being under the control of professional APC, via intercellular "trans" signaling.

Many mechanisms contribute to the escape of tumor cells and virally infected cells from immune surveillance. One of the mechanisms is that these cells lack the costimulatory molecules required for T-cell activation. "Active" immunotherapeutic strategies have been developed that are predicated upon expressing costimulators on tumor cell, and other antigen-presenting cell, surfaces. An alternative "passive" immunotherapeutic approach involves the steps of recovering tumor-infiltrating lymphocytes (TIL) from tumor beds, or T cells from the blood of cancer patients, expanding the numbers of these T cells ex vivo with lymphokines, and injecting them back into the patient.

A major limiting factor for the clinical application of therapeutic T cells is their loss of activity once injected into patients. This is generally believed to be a consequence of a deprivation of T cell activators, such as soluble cytokines and surface costimulators. Costimulation is required not only for the early activation of T cells, but also for the later maintenance of their post-activation effector capacity, referred to as "effector costimulation." In an effort to maintain therapeutic T cells in a fully activated state, activating cytokines, such as IL-2, have been administered systemically to patients receiving therapeutic T cells, albeit with IL-2 toxicities and insufficient therapeutic benefit.

T cells also bear inhibitory receptors. The fate of T cells following T cell receptor (TCR) stimulation is guided by the integration of costimulatory and inhibitory receptor inputs. As indicated, costimulatory ligands on APCs trigger cognate receptors on T cells, with resultant enhancement of T cell proliferation, cytokine secretion, and differentiation. In contrast, binding of inhibitory ligand molecules on various cells to cognate receptors on responding T cells diminishes effector functioning, by inducing T cell unresponsiveness or apoptosis.

Professional antigen-presenting cells (APC), by virtue of the surface costimulatory molecules, are geared towards potent T-cell activation. APC can be converted into deletional APC, or "artificial veto cells", by expressing coinhibitors at their surfaces. This is discussed, for example, in U.S. Pat. Nos. 5,242,687; 5,601,828; and 5,623,056. Such coinhibitors bind to coinhibitor receptors on cells, leading to T-cell inactivation.

One approach for expressing costimulators and coinhibitors on APC, such as tumor cells, is gene transfer. When used for APC and tumor cell engineering, gene transfer techniques have shortcomings. For example, APCs, including tumor cells, are often poorly transfectable. In addition, transfection proceedings are cumbersome and time-consuming. Furthermore, expressing more than a costimulator (or coinhibitor) is difficult. These and other issues have impeded the widespread application of gene therapy for APC and tumor cell engineering.

Protein transfer offers a number of advantages over gene transfer for engineering APCs and other cells. These advantages include the ability to modify poorly transfectable cells (for example, biopsy-derived tumor cells), the simplicity of expressing multiple proteins on the same cell surface, and the relative ease and rapidity of the procedure. The successful use of recombinant GPI-modified costimulator and MHC protein derivatives for protein transfer has been reported. (See, Brunschwig, et al. J. Immunol., 155:5498 (1995); McHugh, et al; Proc. Natl. Acad. Sci. USA, 92:8059 (1995); and McHugh, et al. Cancer Res., 59:2433 (1999)). A shortcoming of the GPI protein transfer strategy, however, resides in scaling up the purification of GPI proteins from membranes of transfected cells. The successful use of protein conjugates consisting of recombinant Fc-modified costimulator derivatives complexed to palmitated protein A for protein transfer has also been reported (See, U.S. Pat. No. 6,316,256; Chen, et al. J. Immunol., 164:705 (2000); Zheng, et al. Cancer Res., 61:8127 (2001)). Yet another protein transfer method entails appending $his_6$-tagged costimulators to cells pre-treated with the chelator lipid, NTA-DTDA, whose NTA groups bind the hexahistidine tags (See, van Broekhoven et al. J. Immunol., 164:2433 (2000)).

Kim and Peacock, J. Immunol. Methods, 158:57 (1993), report the use of palmitate-conjugated protein A for coating cells with artificial receptors which facilitate intercellular interactions. More specifically, a method is reported for attaching an antibody onto the surface of a cell using palmitated protein A. The article does not teach use of a lipidated protein for attachment of anything other than an antibody to a cell. As such, their modified cells serve only as artificial receptors for antigens.

Phillips et al., *Immunity*, 5:163-172 (August, 1996) report the preparation of a fusion protein using a CD8 leader segment, the Fc domain, of immunoglobin and the ectodomain of a type II membrane protein, CD94. The present transfer methods are applicable to both type I and type II proteins and are neither taught nor suggested in the article.

Darling, et al., *Gene Therapy*, 4(12):1350-60 (December 1997) report the use of a biotin/avidin-based system for protein transfer. This method involves biotinylation of the target cell, attachment of an avidin group to the protein to be transferred, and combining the biotinylated target cell and the avidin-tagged protein. This method has significant limitations, including its dependence on covalent modifications that could perturb multiple proteins on cell surfaces.

Certain T cell costimulators, including B7-1, B7-2,4-1BB ligand, and OX40 ligand, are expressed on T cells themselves, either under normal conditions or in diseased states (See, Carreno et al. Annu. Rev. Immunol., 20:29 (2002); Nakamura et al. J. Exp. Med., 194:629 (2001); Kochli et al. Immunol. Lett., 65:197 (1999); Wolthers et al. Eur. J. Immunol., 26:1700 (1996); Takasaki et al. Intern. Med., 38:175 (1999); Weintraub et al. J. Immunol., 159:4117 (1997); Weintraub et al. Clin. Immunol., 91:302 (1999)). In addition, it is known that T cells can acquire costimulators from APC via intercellular transfer (See, Hwang et al. J. Exp. Med., 191:1137 (2000); Sabzevari et al. J. Immunol., 166:2505 (2001)), just as they can acquire MHC:peptide antigen complexes via intercellular transfer (See, Lorber et al. J. Immunol., 128:2798 (1982); Hudrisier et al. J. Immunol., 166:3645 (2001)). These costimulators and MHC:peptide antigen complexes on T cells have been presumed to trigger cognate receptors on neighboring T cells in trans.

After T cell triggering, first the inhibitory receptor Fas, and then its cognate ligand, Fas ligand, are sequentially upregulated on T cell surfaces. While some have surmised, on the basis of indirect evidence, the possibility that T cell "suicide" (as a concomitant of T cell "fratricide/sororicide") might result from such Fas ligand:Fas pairing at the cell surface (See, Brunner et al. Nature, 373:441 (1995); Dhein et al. Nature, 373:438 (1995); Ju et al. Nature, 373:444 (1995)), definitive proof that this mechanism is indeed operative (for example, enforced expression of the ligand:receptor pair) is lacking. Furthermore, while there are other examples of ligand:receptor pairs that are naturally co-expressed on T cell surfaces, for example, CD58 (LFA-3) and its cognate receptor CD2 (See, Springer et al. Annu. Rev. Immunol., 5:223 (1987)), the functional implications of this pairing at the same cell surface (for example, the potential for continuous triggering and/or competitive blockade of incoming trans signals) have been ignored.

The concept of "autocrine signaling", wherein a cell secretes a soluble protein ligand that binds and signals through one of its own native receptors, has been discussed in the prior literature (See, e.g., Hoffbrand A. V., *Semin. Hematol.*, 30:306 (1993). For example, certain leukemia cells secrete soluble growth factors that can bind to the cell's own receptors, prompting the notion that autocrine signaling results from this ligand:receptor interaction and may play a role in leukemogenesis. However, this literature has dealt exclusively with soluble ligands which bind to the cell's receptors. No therapeutic cells in the art have been designed with membrane-embedded proteins with the capacity to trigger their own activating or inhibitory receptors.

There remains a need, therefore, for methods of efficient and quantitative transfer of proteins and peptides to cells. A further need is to provide such methods in which immunoregulatory or other molecules that retain their function can be attached to cells of interest, including membrane-binding proteins that enable cells to auto-stimulate themselves.

SUMMARY OF THE INVENTION

The present invention has met the above needs, by providing methods for quantitative transfer of a domain having trans-signaling and/or adhesion function onto a cell surface. Typically, the domain will be the extracellular domain having one or both of these functions. In a preferred embodiment, the extracellular domain of an immuno-regulatory molecule is used. More specifically, the present methods provide a two-step protein transfer approach, which permits delivery of graded amounts of proteins to a cell surface. The methods utilize a fusion protein comprised of at least two domains, one of which preferably encodes a molecule having immunoregulatory function. By adding the fusion protein to cells coated with a lipidated protein, fine titration of, for example, the immunoregulatory molecule's extracellular domain is achieved.

The present protein transfer methods have wide application. For example, the methods have been used to establish that costimulator thresholds exist, and that the levels of surface costimulator on APC can dictate both the magnitude and the quality of evoked T-cell responses. The present methods are also applicable to the generation of cancer vaccines; these vaccines show significant anti-tumor effects in vivo. Furthermore, the methods can be used to generate artificial veto cells, expressing one or more coinhibitors, that can be used to delete pathogenic T-cells. Cells produced according to the present methods are therefore useful in the treatment of cancer and also in the treatment of autoimmune diseases. The methodologies described herein can also be used in the establishment of animal models and for the study of immunological issues regarding, for example, T-cell activation, use of costimulators to override apoptotic signals, function of coinhibitors versus costimulators, synergy of costimulators used in the treatment of cancer, and use of coinhibitors in the treatment of autoimmune diseases.

In an additional aspect, the present invention provides a method of producing therapeutic cells coated with one or more extrinsic protein ligands that can not only trigger cognate receptors on neighboring cells (trans signaling), but also stimulate themselves via interaction of the ligand with a receptor on the cell's own surface (cis signaling). As used herein, "cis signaling" refers to the receptor:ligand interaction on the surface of a cell that provides signals to the interior of that cell, such signals triggering protein phosphorylation or dephosphorylation, DNA transcription or other cellular events. As described above, such cells have wide application and can be used in the treatment of many diseases, including cancer and autoimmune diseases. The fusion proteins can be coated on the cell surface in a two step method, as described above, or can alternatively be applied in a one-step method, by painting a fusion protein having a domain of a molecule, such as a glycophospholipid, which is capable of incorporating into the cell membrane directly. Such a fusion protein would have, as a second domain, the signaling protein of interest.

It has been discovered that when ligands of interest are immobilized on the cell surface, surprisingly, they are still capable of binding with the cognate receptor on the same cell and providing the stimulation or inhibition necessary to activate (or turn off) the cells. This was not expected, based on the prior art. Moreover, it has been found that the enforced ligand: cognate interaction can give a much stronger interaction than that found with intercellular trans signaling.

For example, in the case of T cells of the immune system, use of an activating protein renders the therapeutic T cells suitable for use in the treatment of cancer and virally mediated diseases, whereas use of an inhibitory protein renders the therapeutic cells suitable to function as regulatory T cells for treatment of autoimmune and alloimmune disorders. Therapeutic auto-stimulating cells, corresponding to numerous other immune and non-immune cell types (including various stem and progenitor cells) can be similarly configured.

The present invention further provides methods for making the present therapeutic auto-stimulating cells, and methods for using these cells in the study and treatment of cancer, viral, autoimmune and alloimmune diseases, as well as any one of a number of conditions in which auto-stimulating cells may be beneficial. Other methods for studying and treating these diseases and conditions, both in vivo and ex vivo, are also disclosed.

It is therefore an aspect of the invention to provide novel therapeutic cells that have the capability of auto-stimulating themselves.

Another aspect of the present invention is to provide methods for producing such auto-costimulating cells, with protein transfer being a preferred method for achieving this end.

Yet another aspect of the present invention is to provide therapeutic cells for the study and treatment of cancer, viral, autoimmune and alloimmune diseases and disorders, as well as any one of a number of conditions in which auto-stimulating cells may be beneficial.

These and other aspects of the invention will be apparent based upon the following description and appended claims.

DETAILED DESCRIPTION OF THE INVENTION

Figure 1:
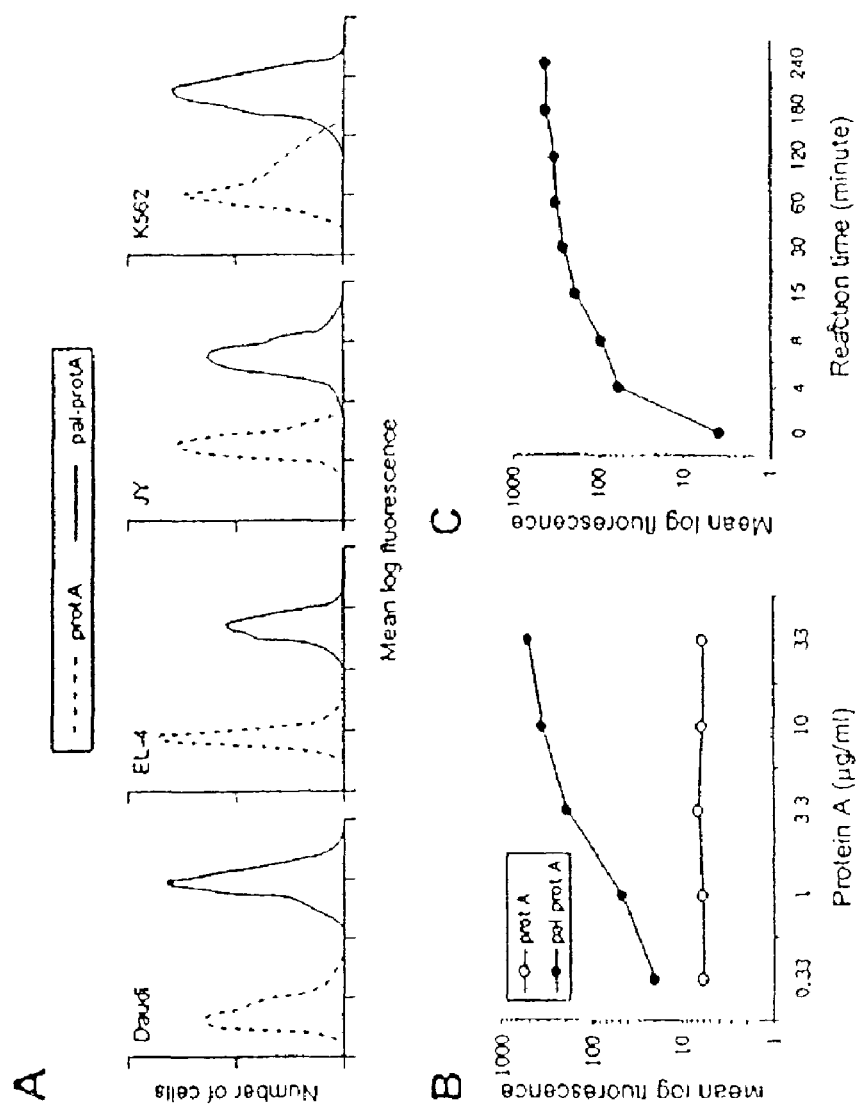
FIG. 1, including 1A, 1B and 1C, demonstrates the efficacy of coating cells with a lipidated protein, according to the methods of Example 1.

The present invention is directed to methods for transferring one or more proteins to a cell, generally comprising the steps of coating the surface of a cell with a first protein, which is a lipidated protein, and contacting the coated cell with a second protein, which is a fusion protein. The fusion protein is comprised of a first domain having affinity for the lipidated protein and a second domain of a peptide, protein, or derivative or fragment thereof, having trans signaling and/or adhesion function. Preferably, the extracellular domain is used, and the second domain has immunoregulatory function. "Derivative", as used in reference to peptides and proteins, refers to variants of peptides and proteins such as analogues wherein, for example, one or more amino acids within the peptide chain has been deleted, added or replaced with an alternative amino acid. A "fragment" refers to a portion of the amino acid sequence of a peptide or protein. It will be understood that "derivatives" and "fragments" of peptides and proteins retain the physiological function of the wild type peptide or protein and thus are biologically active.

The present methods are applicable to any cell having a lipid bilayer membrane. For example, any kind of a patient's autologous cells can be used, harvested by any means known in the art. Use of any allogeneic mammalian cell line is also within the scope of the present invention. Examples of allogeneic cell lines suitable for use in the present invention include, but are not limited to, EL-4 cells (mouse thymoma cells), 293 cells (human kidney cells), K562 cells (human leukemia cells), Daudi cells (human B cell line) and JY cells (human B cell line). These cells are commercially available from the American Type Culture Collection, Manassas, Va. Non-commercially available cell lines are also within the scope of the present invention. Use of isogeneic and xenogeneic cells is also within the scope of the present invention.

Any protein that can be lipidated is suitable for use in the present methods. Examples include, but are not limited to, protein A and protein G, both of which are commercially available. Similarly, any lipid can be used to prepare the lipidated protein. Lipids having carbon chains between about 12 and 22 are preferred, with a carbon chain of 16 (palmitate) being most preferred. The length of the lipid chain can be varied based upon the needs and desires of the user. It will be understood to those skilled in the art that the lipidated portion of the first protein will become attached to or incorporated into the phospholipid bilayer that makes up the membrane of the cell, and that this is what is meant by the phrase "coating the surface of the cell" as that phrase is used herein.

The amount of lipidated protein used to coat the cell may also vary based on the needs and desires of the user, and based on the particular lipid and particular protein selected. Preferably, enough lipidated protein is used to coat the entire cell. This amount will typically be at least about 30 micrograms of lipidated protein for every $5 \times 10^6$ cells.

Following coating of the cells, the cells are then contacted with a second protein. The second protein is a fusion protein in which two different domains have been fused, such as through recombinant DNA technology standardly used in the art, to create a single DNA sequence. The first domain can be attached at either the amino terminus or the carboxyl terminus of the fusion protein. The first domain encodes a peptide, protein, or derivative or fragment thereof, what has affinity for the lipidated protein. Thus, the protein used in the lipidated protein is ideally selected in conjunction with the protein encoded by the first domain of the fusion protein, so that proteins having affinity for one another are used. Affinity between the proteins can be determined by Biacore technology or other methods familiar in the art. Because of this affinity, the fusion protein binds to the lipidated protein, which has already been incorporated into the cell membrane. In this manner, the fusion protein is transferred to the cell. A particularly preferred combination uses a palmitated protein A and a first domain encoding an Fc region. For example, the Fc region of human immunoglobulin GI (IgG1), designated $Fc\gamma_1$, can be used. Other suitable first domains in the fusion protein include leucine zipper protein domains and single-chain Fv derivative domains.

The second domain of the fusion protein encodes a peptide, protein, or derivative or fragment thereof, having immunoregulatory function and capable of trans signaling to a second cell. Examples include, but are not limited to, costimulators and coinhibitors. Any suitable costimulator can be used including but not limited to B7-1, B7-2, CD48, ICAM-1, ICAM-2, ICAM-3, LFA-3, CD30 Ligand (CD30L), CD40 Ligand (CD40L), 4-1BB Ligand (4-1BBL), OX40 ligand, CD70, CD24, and heat stable antigen. Similarly, any suitable coinhibitor can be used including, but not limited to, CD8, FasL, PP14 and TRAIL.

Significantly, the fusion protein of the present invention can be either a type I or type II protein. Methods for transferring a type II protein to a cell have never been reported. Because the methods of the present invention are equally applicable to type I and type II proteins, they provide a significant advance over the art. Examples of type I membrane proteins include B7-1, B7-2 and CD48; examples of type II membrane proteins include Fas ligand (FasL or CD95L), CD40L, and 4-1BBL. For the type II proteins, the first domains are fused at the carboxyl termini of the type II proteins in order to preserve the functional ends of the molecules. These lists are not exhaustive of the costimulators, coinhibitors and other proteins that can be transferred according to the present invention; the lists reflect all forms of the various molecules including, but not limited to, human and murine forms.

Another significant advance provided by the present methods is that following transfer of the fusion protein to the cell, the portion of the fusion protein having trans signaling function retains this function. Thus, the cells prepared according to the present methods are capable of eliciting an immune response by binding to, and trans signaling through a counter-receptor on a second cell.

In addition, more than one fusion protein can be used to coat a single cell. In this manner, two, three, four, or more trans signaling, for example, immunoregulatory proteins, can be transferred to a cell. In the case of costimulators and coinhibitors, combinations of such proteins can be chosen to have the greatest immunological effect; combinations having additive or even synergistic benefits can be selected and used according to the present methods.

The present methods are further unique in that proteins can be delivered to a cell's surface in a quantitative manner. As noted above, it is preferred to use enough lipidated protein to fully coat the cell. The amount of fusion protein that becomes transferred to the cell is therefore determined by the amount of fusion protein used to contact the coated cell; thus the amount of fusion protein is the limiting or determinative factor. When using more than one fusion protein, predetermined ratios of fusion proteins can be used to contact the coated cell; protein will be transferred to the cell in these approximate ratios.

The present methods can be effected either in vivo or in vitro. In in vivo methods, the lipidated protein and the fusion protein are injected directly into a patient. The injection can occur sequentially (with the lipidated protein first) or concurrently, with premixing of the lipidated protein and the fusion protein(s). Injection can be localized, for example, intra-tumoral, or systemic, for example, into a vessel. The present methods, and cells produced thereby, in contrast to other art-reported methods, have particularly high protein stability, making the present method practical for in vivo application. In vitro methods involve the extraction of cells from a patient, and the subsequent coating and contacting of the cells; alternatively, commercially obtained allogeneic cells can be used. In either case, the treated cells can then be injected into a patient.

All of the above descriptions relating to cell type, first proteins, second proteins, and in vivo, in vitro and other delivery techniques apply equally to all embodiments of the invention disclosed herein.

The present invention is further directed to methods for determining costimulator activation thresholds in T-cells. These methods generally comprise transferring one or more fusion proteins to a cell, in the manner described above. The cells to which protein has been transferred are then mixed with T-cells. T-cells can be, for example, harvested from peripheral blood mononuclear cells by methods known in the art. T-cell proliferation, if any, can be measured, as can cytokine secretion levels according to means known in the art, such as those described in the Example section.

The present invention is further directed to methods for treating an illness using the present protein transfer technology. These methods generally comprise administering to a patient an effective amount of the cells prepared in vitro according to the method described above, or administering the proteins in vivo. The method can be performed by either in vivo or in vitro protein transfer of the fusion protein(s) to the target cells. For in vitro methods, either extracted autologous cells or allogeneic cells are coated with a lipidated protein and contacted with one or more fusion proteins. An effective amount of these cells are then administered to a patient. For in vivo methods, lipidated protein and one or more fusion proteins are administered to a patient in an amount sufficient to result in transfer of an effective amount of fusion protein(s) to an effective amount of cells.

"Illness" as used herein refers to cancer, viral, and autoimmune and alloimmune diseases, including but not limited to melanoma, ovarian cancer, breast cancer, colon cancer, pancreatic cancer, hepatic cancer, lung cancer, glioblastoma multiforme, prostate cancer and leukemia; viral infections, such as chronic viral infections with HBV, HCV, HTLV-1, HTLV-II, EBV, CMV, HSV-I, HSV-II, and KSHV; arthritis, rheumatoid arthritis, asthma, graft-versus-host disease, organ rejection, systemic lupus erythematosis, atopic allergy, inflammatory bowel disease, multiple sclerosis and allergic dermatitis. The methods are particularly applicable to treatment of cancer, in that the lipidated protein and fusion protein(s) in the in vivo methodology, or the coated and contacted cells in the in vitro methodology, can be directly injected into one or more tumors of the patient. "Patient" is used herein to refer to members of the animal kingdom, including humans. The present methods are generally applicable to patients capable of generating at least a minimal immune response.

An effective amount of cells produced by the present protein transfer methods should be used in the present treatment methods. The effective amount is that amount of cells that will deliver the amount of protein to a patient needed to bring about a desired result. Generally, the desired result can be, for example, stimulation of an immune response or suppression of an immune response. In the case of cancer treatment, an effective amount would be that amount which would protect a patient against tumor growth or reduction, if not elimination, of tumors. In the case of autoimmune or alloimmune disease, an effective amount would be that amount which would alleviate if not eliminate one or more symptoms of the autoimmune or alloimmune disease being treated. In the case of treatment of viral diseases, an effective amount would be that amount which would induce a reduction, if not elimination, of the viral infection. It will be understood that the effective amount will vary from patient to patient depending on such factors as the patient's size, the condition of the patient's immune system, the patient's ability to mount an immune response, and the type and severity of the illness. The appropriate effective amount for each patient can be determined by one skilled in the art, and will generally be at least about $10^7$ modified cells or 100 μg Fc fusion protein intratumorally. In the case of auto-stimulated T cells, described more fully below, the effective amount will generally be at least about $10^8$ modified cells. The present invention is further directed to a cancer vaccine comprising cells prepared according to the present protein transfer methods contained in a suitable carrier. Any suitable carrier can be used, provided compatibility problems do not arise. Examples include PBS, and serum-free medium. The vaccine can include a variety of fusion proteins; different cells each having a different fusion protein, or cells having more than one fusion protein attached thereto, can be used for example. Thus, a "cocktail" of immunoregulatory proteins can be contained in the present vaccines, and can be introduced to a patient according to the present methods. The particular immunoregulatory proteins to use in a cocktail can be determined by one skilled in the art based upon such factors as the patient being treated and the type and severity of the patient's illness. Different combinations could be used to treat different types of tumors. The cocktail can be pre-mixed and injected into a tumor bed, thereby leading to tumor suppression. The vaccines have been found effective in both pre-immunizing recipients against a subsequent tumor challenge and in the treatment of established tumors.

The present invention is further directed to methods for enhancing the efficacy of therapeutic cells by transferring proteins to the surface of cells to provide auto-stimulating ability. The method generally comprises coating the surface of a cell with a first protein, the first protein being a lipidated protein, and contacting the cell with a second protein. The second protein is a fusion protein comprised of a first domain having affinity for the first protein and a second domain having cis signaling function, and is capable of binding to a receptor on the cell's own surface.

In an alternative one-step embodiment, also preferred, the method of transfer comprises coating the surface of a cell with a fusion protein having a first domain and a second domain, the first domain capable of becoming incorporated into a membrane of a cell, and the second domain capable of binding to a receptor on the cell's own surface. The first domain of the fusion protein of the one-step method will preferably by a glycophospholipid, more preferably glycosyl phosphatidylinositol (GPI). The second domain will comprise the protein of interest, such as the costimulators and inhibitors described above.

The fusion protein transferred to the surface of the cell is a ligand that binds to a receptor on the same cell, and in so doing, engenders a change in the physiological state of the cell. "Auto-stimulating cell" or "auto-stimulating ability" as used herein refers to a cell bearing on its surface an extrinsic ligand, generally a protein, capable of engaging and triggering a receptor on its own surface. Such engagement of the ligand:receptor on the cell surface results in a cis signal as that term is defined above; such a signal will include stimulatory signals and inhibitory signals, as those terms are understood in the art. Thus the terms "auto-stimulating" and "cis signaling" refer to both stimulatory and inhibitory outcomes from the receptor: ligand interaction. The present invention stems from the discovery that if one paints a ligand onto cognate receptor-bearing cells, receptor triggering can ensue.

Preferred embodiments of the present invention are within the immunotherapeutic realm. In a preferred embodiment, the present invention comprises the painting of a patient's autologous T cells with proteins, for purposes of maintaining these cells in an activated state after they are injected back into a patient. This is especially useful for enhancing the activity of therapeutic T cells with anti-tumor or anti-viral properties. For purposes of activating T cells in this context, any suitable costimulator can be used including, but not limited to, B7 family costimulators (such as B7-1, B7-2, B7-h/B7rp-1), 4-1BB ligand, OX40 ligand, LIGHT, CD70, CD24, CD48, ICAM-1, ICAM-2, ICAM-3, LFA-3, and CD30 ligand.

In another embodiment, the present invention comprises painting a patient's autologous dendritic cells with proteins, for purposes of stimulating their proliferation and/or differentiation. For purposes of dendritic cell activation, any suitable dendritic cell activator can be used including but not limited to CD40 ligand, TRANCE, and Flt-3 ligand, as well as otherwise soluble dendritic cell activators that retain their function when immobilized on the cell surface, for example, glycosyl-phosphatidylinositol-modified GM-CSF. According to other embodiments of the present invention, any one of a number of other cell types can be similarly painted to enhance their proliferative or other functional capacities, either in vivo or ex vivo, in beneficial ways. Different cell types that can be used include, for example, lymphokine-activated killer cells, monocytes, B cells, natural killer cells, neutrophils, eosinophils, basophils, mast cells, as well as stem and progenitor cells, including hematopoietic stem cells, mesenchymal stem cells, embryonic stem cells, keratinocytes, endothelial cells, islet cells, fibroblasts, osteoblasts, muscle cells, and neural cells. This list is not meant to be limiting.

One-step or two-step protein transfer methods as described above are preferred methods for expressing extrinsic proteins on the surfaces of the present cells for purposes of cellular auto-stimulation. Any protein that can be produced in a lipidated form and that therein has the capacity to incorporate into a cell membrane (for example, a recombinant glycosyl-phosphatidylinositol-modified protein), or that can bind to a second protein that has the capacity to incorporate into a cell membrane (for example, a recombinant immunoglobulin Fc-modified protein that can bind to membrane-incorporating palmitated-protein A; or a recombinant $his_6$-tagged protein that can bind to the membrane-incorporating chelator lipid, NTA-DTDA), is suitable to be used as a protein paint for coating the present cells. As used herein, the term "extrinsic protein" will refer to those fusion proteins that are transferred to the surface of the cell using the protein transfer methods described above.

The amount of protein used to paint the cells is as described above.

Gene transfer methods can also be used according to the present invention for expressing exogenous proteins with auto-stimulatory potential on the surfaces of the present cells. Genetic sequences encoding these proteins can be introduced into cells ex vivo by any one of a number of transfection modalities, and these transfected cells can be administered to a patient as therapeutic cells, according to methods well known in the art. "Genetic sequence" refers to a polynucleotide comprising the coding sequence for a defined protein and associated regulatory and other non-coding sequences. Genetic sequences in the form of cDNA clones are commercially available for a wide array of genes. Moreover, for those cDNA clones that are not readily accessible from commercial and other sources, knowledge of their nucleotide sequences can be used to easily reproduce their cDNAs via the reverse-transcriptase polymerase chain reaction method, incorporating the relevant gene sequences into the primers.

Transfection methods in the art encompass a host of vectors for delivering therapeutic genes, a host of transcriptional and translational regulatory elements that can be appended to the gene of interest, methods for producing and using these vectors, and methods for monitoring therapeutic gene efficacy and toxicity. Significantly, inducible promoters are known in the art for regulating the expression of the transfected gene, so that levels of the encoded protein can be regulated. Those inducible promoters that can be regulated with orally-administered drugs are especially useful in this context. The use of transfected cells as therapeutic cells in this way for the treatment of experimental osteoarthritis is described in Pelletier, Arthritis and Rheumatism, 40:1012-1019 (1997), wherein transfected synovial cells were re-injected back into diseased joints. This is also illustrated by Yasuda, J. of Clinical Investigation, 102:1807-1814 (1998) who described the treatment of autoimmune diabetes with transfected islet cells.

According to yet another embodiment of the present invention, gene transfer can be used to transfer genes encoding not just a ligand, but also a receptor on the present cells, with the receptor chosen by virtue of its capacity to bind to native or extrinsic ligands on said cells.

Another significant advance provided by the present compositions and methods is that following injection of the therapeutic cells into patients, the stimulatory effect mediated by the protein ligands, transferred via coating or gene transfer, persist for some period of time. Where protein transfer is used to transfer the proteins, stimulation of the cells will eventually decrease with time, for example, as a consequence of dilution resulting from repeated cell divisions; in many contexts, this progressive decrement constitutes an advantage since long-term triggering is often not desirable. Where gene transfer is used to provide exogenous gene expression, expression can be maintained for prolonged periods when suitable expression vectors are chosen, that are well known to those familiar with the art.

In addition, more than one protein ligand can be used to coat a single cell. In this manner, two or more cis signaling proteins (for example, immunoregulatory proteins) can be transferred to a cell surface. In the case of costimulators, combinations of such proteins can be chosen to have the greatest immunological effect; combinations having additive or even synergistic benefits can be selected and used according to the present compositions and methods. Also, given the quantitative control afforded by protein transfer methods, where the amount of protein that becomes transferred to the cell is determined by the amount of protein used to contact the painted cell, predetermined ratios of the proteins to be painted can be achieved.

Another advantage of the present methods stems from the enforced proximity of the ligand and its receptor on the same cell surface. For certain ligand:receptor pairs, for example, the costimulator B7-1 and its receptor CD28, there is a fast off-rate, which tends to limit intercellular trans costimulatory signaling. By contrast, the cells of the present invention feature ligand and receptor anchored to the same cell surface, which by the mass action law tends to stabilize the interaction between these "locked-in" binding partners, forced into sustained proximity. Thus, the present invention provides for an entirely new mode and kinetics of ligand:receptor signaling.

The present methods can be effected either in vivo or ex vivo. In ex vivo methods, the desired cells are isolated from a sample of a patient's blood or tissues, painted with the extrinsic protein or transfected with a gene encoding a protein of interest with auto-stimulatory potential, and then re-infused into the patient. Additional manipulations of the present cells are possible during the ex vivo step, for example, cytokine treatment and amplification of cell numbers. In vivo methods involve the infusion into a patient of a fusion protein that comprises both a homing element, that attaches the protein to the desired cell in vivo, and a ligand element, that triggers a receptor on the same cell in cis. Preferred homing elements are Fv domains of immunoglobulin proteins or cytokines with sufficient affinity for cognate surface receptors on the target cells. The single polypeptide chain derivative comprising the Fv region of an immunoglobulin molecule (scFv), for example of an immunoglobulin IgG1 molecule, can also be used as a first domain. Specific examples of scFv include ones with specificities for cytokine and other receptors (for example, HER-2/neu), carcinoembryonic antigen (CEA), prostate specific antigen (PSA), CD33 and AIRM1. HER-2/neu receptors are another preferred target on cancer cells, since they are found on epithelial carcinomas of the breast and ovary. CEA is highly expressed on gastrointestinal tumors, including colon cancer, and immunoinhibitory properties have been attributed to it. PSA is highly expressed by most epithelial prostate carcinomas. CD33 and AIRM1 are sialoadhesin family members expressed on cells of the myelomonocytic lineages. Ligation of CD33 or AIRM1 on chronic myeloid leukemia cells with antibodies decreases cell proliferation and survival. As used herein, the term "homing element" refers to a protein or other molecule than can bind to receptors on specific cells, and, when administered to a patient, attach to the cells of interst.

All of the above descriptions relating to cell type, protein ligands, protein receptors, protein and gene transfer methods, and ex vivo and in vivo and other delivery techniques apply equally to all embodiments of the invention disclosed herein.

The present invention is further directed to methods for determining receptor activation thresholds and other functional properties of the present cells. For example, in the case of T cells, T cells can be painted with different costimulators and their respective effects on TCR activation thresholds can be compared. In addition, costimulator-painted T cells can be used as cellular reagents to evaluate the relative activities of different T cell modulatory agents. As another example, T cells can be painted with membrane-incorporating major histocompatibility complex (MHC) protein:peptide antigen (or lipid antigen) conjugates, which can trigger TCR on the same cells. In turn, these antigen auto-stimulated T cells can be used to test effects of extrinsic agents on TCR and costimulator receptor activation thresholds, as well as any one of a number of other T cell physiological endpoints.

The present invention is further directed to methods for treating an illness using the present cellular auto-stimulation technology. These methods generally comprise administering to a patient an effective amount of the cells prepared ex vivo according to the method described above, or administering fusion proteins that auto-stimulate cells that they home to in vivo. For the ex vivo methods, cells are coated with a lipidated protein or a membrane-incorporating protein conjugate. An effective amount of these therapeutic cells are administered to a patient. For the in vivo methods, one or more of said fusion proteins is administered to a patient in an amount sufficient to result in transfer of an effective amount of this protein(s) to an effective amount of cells.

Administration can be by any means known in the art, such as by intravenous injection. The auto-stimulating cells as described herein can be contained within a suitable pharmaceutical carrier for administration according to the present methods. "Suitable pharmaceutical carrier" is as described above.

EXAMPLES

The present examples are intended to illlustrate the invention and should not be construed as limiting the invention in any way.

Example 1

The following example demonstrates a method for transferring a B7-1•Fcγ$_1$ fusion protein to a cell using palmitated protein A.

Palmitation of Protein A

Recombinant protein A (Calbiochem, La Jolla, Calif.) was derivatized with the N-hydroxysuccinimide ester of palmitic acid (Sigma, St. Louis, Mo.) as described by Kim and Peacock, *J. Immunol Methods*, 158:57 (1993). Briefly, a stock solution of the N-hydroxysuccinimide ester of palmitic acid was made, as was a solution containing protein A in a concentration of about 1.5 mg/ml. The solutions were mixed in a ratio of about 10 μg ester per ml protein and incubated at room temperature with constant mixing for about 18 h. The lipid-derivatized protein A was purified as described by Huang, et al., *J. Biol. Chem.*, 225:8015 (1980) using a 30-ml Sephadex G-25 (Sigma) column. The protein product, referred to herein as "pal-prot A○, was quantitated using a bicinchoninic acid kit (Bio-Rad, Richmond, Calif.), filter sterilized, and stored at 4° C. until use.

Membrane Incorporation of pal-prot A

Daudi EL-4, JY and K562 cells (3-7×10$^6$/ml) were separately resuspended in RPMI 1640 medium (BioWittaker, Walkersville, Md.) after three washes with this same medium. Varying concentrations of pal-prot A (or nonderivatized protein A as negative control) were added to the cell suspension, and the mixture was incubated at 4° C. for 2 h with constant mixing. To assess the incorporation of pal-prot A onto cell surfaces, cells were washed twice in buffer (0.25% BSA/0.01% sodium azide/PBS) and then incubated on ice for 1 h with 100 μl of 100 μg/ml FITC-human IgG (Sigma) diluted with the same buffer. Cells were washed twice in the buffer and analyzed on a FACStar® flow cytometer (Becton Dickinson, Mountain View, Calif.).

In a first set of optimization experiments, efficient incorporation of pal-prot A was documented in four cell lines (FIG. 1A) as detected with FITC-conjugated human IgG. As a negative control, nonderivatized protein A lacked the capacity to bind to the same cells. Data from the FACStar analysis was plotted as arbitrary units of log 10 fluorescence intensity versus number of EL-4 cells; membrane incorporation was dose dependent and started to plateau at about 33 μg/ml pal-prot A, as shown in FIG. 1B. EL-4 cells were incubated with 33 μg/ml pal-prot A for the indicated periods of time and processed as above; pal-prot A incorporation was rapid, appearing immediately after addition to the cells and reaching a plateau at ~1 h, as shown in FIG. 1C. This data demonstrates that numerous different cell lines can be used in the present protein transfer methods, and that the lipidated protein was incorporated into the cell fairly rapidly.

Preparation of Recombinant B7-1•Fcγ$_1$

Figure 2:
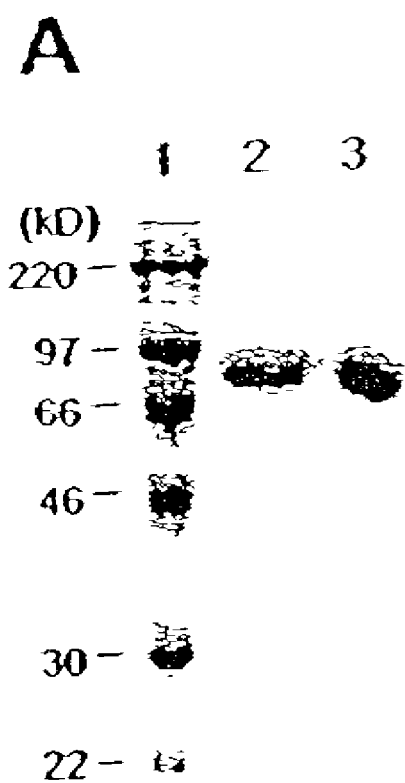
FIG. 2 provides the SDS-PAGE analysis of recombinant B7-1•Fc$\gamma_1$ prepared as described in Example 1.

The expression plasmid pCDM8/B71 g, encoding the complete human B7-1 extracellular domain linked in-frame to the Fcγ$_1$, was obtained from the American Type Culture Collection (Manassas, Va.). The sequence encoding B7-1•Fcγ$_1$ was mobilized from pCDM8/B71 g by digesting with XbaI, filling-in with Klenow fragment, and subsequently digesting with HindIII. The mobilized fragment was subcloned into the EBV episomal expression vector pREP7β (Invitrogen, San Diego, Calif.) with HindIII and filled-in BamHI sites. The plasmid was transfected into 293 cells (human kidney cell line; American Type Culture Collection), and hygromycin B-resistant colonies were selected in serum-free UltraCulture medium (BioWittaker) supplemented with 10 mM glutamine, penicillin/streptomycin, and 200 μg/ml hygromycin B. Secreted B7-1•Fcγ$_1$ was purified from conditioned medium by protein A-agarose (Life Technologies, Germantown, Md.) affinity chromatography and verified by SDS-PAGE. The protein was run on a 10% SDS-polyacrylamide gel and visualized with Coomassie blue as a dominant single band of 80 kDA under both reducing (lane 2) and nonreducing (lane 3) conditions as shown in FIG. 2. Its identity was confirmed by ELISA, with a recombinant protein binding strongly to the human B7-1 specific mAb, BB-1, but not to control Ab (data not shown).

B7-1•Fcγ$_1$ Protein Transfer

Cells precoated with pal-prot A were washed once and resuspended in RPMI 1640 medium (3-7×1$^6$ cells/ml). pREP7B-transfected K562 cells (K562/REP7b) were serially incubated with 33 μg/ml protein A for 2 h, 33 μg/ml Fcγ$_1$ fusion protein for 1 h, and BB-1 as primary Ab and FITC-conjugated goat anti-mouse IgG as secondary Ab. To monitor protein delivery, 10$^6$ cells were washed twice with the same buffer as above, incubated on ice for 1 h with 1 μg of human B7-specific mAb BB-1 (PharMingen, San Diego, Calif.) in 100 μl of buffer. Cells were washed once and immunostained (on ice for 1 h) with 100 μl of 1:100 diluted FITC-conjugated goat F(ab')$_2$ anti-mouse Ig (Boehringer Mannheim, Indianapolis, Ind.) as secondary Ab. Cells were washed once, resuspended in PBS, and analyzed on a FACStar flow cytometer.

Figure 3:
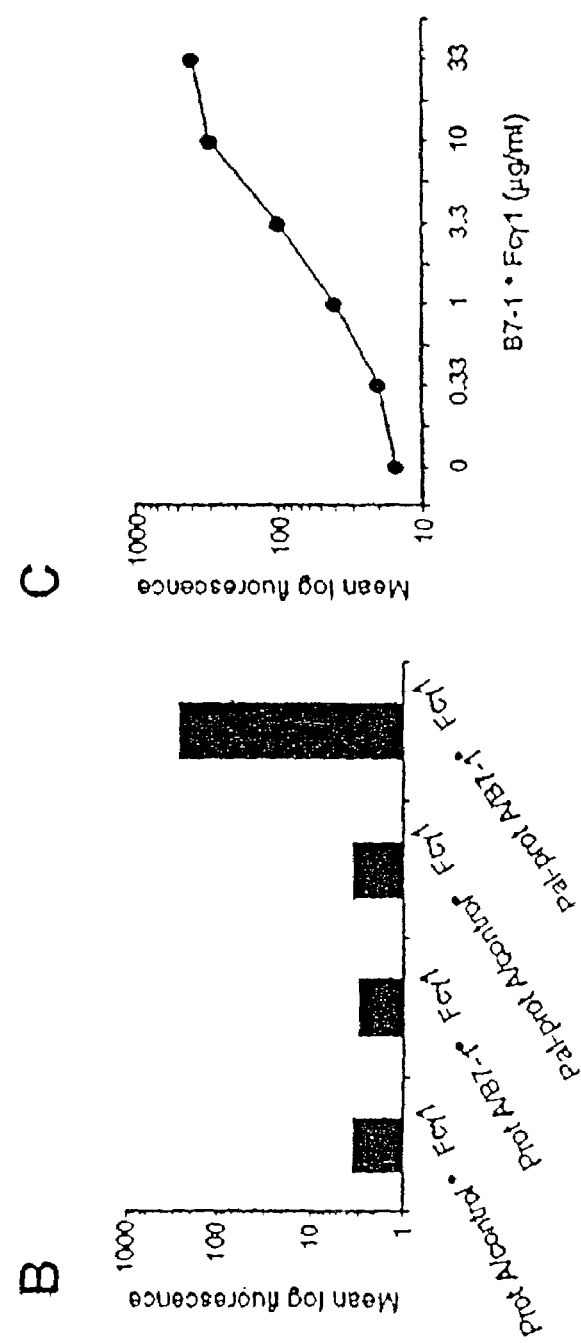
FIG. 3 demonstrates that the present methods achieve fusion protein transfer (FIG. 3A), in a quantitative manner (FIG. 3B), as described in Example 1.

FIG. 3A shows that when K562 cells were precoated with pal-prot A, secondarily applied B7-1•Fcγ$_1$ attached to the cell surface, as detected by immunostaining of the cells with anti B7-1 BB-1 mAb and FITC-conjugated goat anti-mouse IgG. When a control Fc fusion protein (CD28•Fcγ$_1$) was substituted for B7-1•Fcγ$_1$, no BB-1 binding was observed, substantiating BB-1 mAb's B7-1 specificity. When underivatized protein A was substituted for pal-prot A, no BB-1 binding was observed, indicating the dependence of the lipid anchoring for fusion protein attachment.

Quantitation of Exogenously Incorporated B7-1•Fcγ, at Cell Surfaces

Human B7-1•Fcγ, was iodinated using Iodo-beads (Pierce, Rockford, Ill.) according to the manufacturer's protocol, and the labeled protein was purified on a Sephadex G-25 column (Pharmacia, Piscataway, N.J.). The specificity was adjusted to 2.1×10$^6$ cpm/μg by addition of unlabeled B7-1•Fcγl. Protein transfer was performed as described earlier, substituting the labeled protein. All experiments were performed in duplicate. To control for nonspecific binding, excess amounts of unlabeled human IgG (Sigma) were added to specifically block the binding of B7-1•Fcγ$_1$ to protein A. After repeated washing, counts in cell pellets were determined using a gamma counter (1272 Clinigamma; LKB Instruments, Gaithersburg, Md.). Counts resulting from specific binding of B7-1•Fcγ$_1$ were calculated by subtracting nonspecific counts obtained with human IgG. The average number of molecules on a single cell was calculated according to the formula $A \times B^{-1} \times C^{-1} \times N_A$, where A is the determined radioactivity (cpm) in the cell pellet, B is the specific activity of the labeled protein expressed as cpm/mol, C is the number of cells in the cell pellet, and $N_A$ is Avogadro's constant.

As shown in FIG. 3B, when K562 cells were precoated with excess amounts of pal-prot A (33 μg/ml), surface levels of B7-1•Fcγ$_1$ were dependent on the concentrations of applied B7-1•Fcγl. Surface B7-1 epitope levels started to plateau at 33 μg/ml, and the epitope density was similar to that on B7-1 transfected K562 cells (data not shown). The average number of B7-1•Fcγ$_1$ painted per cell was determined using $^{125}$I-labeled B7-1•Fcγl. Again, K562 cells incorporated increasing amounts of B7-1•Fcγ$_1$ as the reagent concentration was increased during the painting process, as shown in Table I.

TABLE I

Painting of B7-1 · Fcγ$_1$ onto K562 cells

| B7-1 · Fcγ$_1$ (μg/ml)[a] | No. of B7-1 · Fcγ$_1$/cell[b] (mean ± SD) |
|---|---|
| 0.033 | 460 ± 240 |
| 0.33 | 9,900 ± 1,200 |
| 3.3 | 92,000 ± 8,300 |
| 33 | 460,000 ± 34,000 |

[a]The final concentration of B7-1 · Fcγ$_1$ present during the painting procedure.
[b]Values were determined as described in Materials and Methods. Specific activity of $^{125}$I-labeled B7-1 · Fcγ$_1$ is 2.1 × 10$^6$ cpm/μg.

At the lowest concentration used (0.033 μg/ml), ~460 molecules became anchored onto each K562 cell. At the highest concentration used (33 μg/ml), about 460,000 B7-1•Fcγ$_1$ molecules became incorporated. Taken together, these data establish that B7-1•Fcγ$_1$ can be applied to pal-prot A-coated cells in a quantitative fashion.

Proliferation Assays

PBMC were isolated from fresh whole blood by Ficoll density centrifugation. T-cells were purified by two rounds of treatment with Lympho-kwik (One Lambda, Canoga Park, Calif.). T-cell purity was verified by lack of a proliferative response to phytohemaglutin ("PHA○") or PMA in the absence of accessory cells. The human CD3-specific mAb HIT3a (PharMingen) was bound to 96-well plates at the indicated concentrations and used in this form to provide a first activating signal to T-cells. Alternatively, PHA was used in soluble form as a source of a first signal. K562 cells transfected with the negative control vector pREP7β (K562/pREP7β) were precoated with pal-prot A and secondarily coated with B7-1•Fcγ$_1$. For each proliferation assay, 1×10$^5$ T-cells were incubated with 4×10$^4$ B7-1•Fcγ$_1$-coated and mitomycin C-treated K562/REP7β cells for 60 h at 37° C. Wells were pulsed with 1 μCi [$^3$H]thymidine for the last 16 h of the incubation period. Cells were harvested and counted on a Betaplate liquid scintillation counter.

Figure 4:
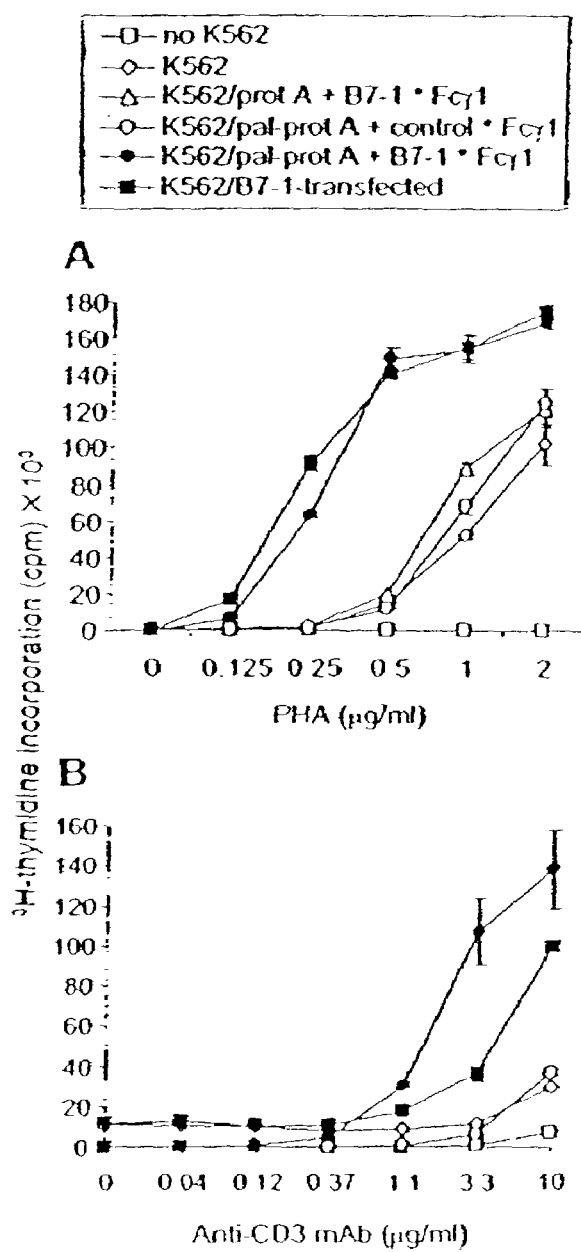
FIG. 4 demonstrates the stimulation of T-cell proliferation in the presence of various proteins (as indicated) using either PHA (FIG. 4A) or anti-CD3 mAb (FIG. 4B) as a first signal, as described in Example 1.

In the proliferation assays, PHA and B7-1•Fcγ$_1$-coated K562/REP7β cells (i.e., K562 cells stably transfected with the pREP7β EBV episomal expression vector) were used to provide first and second signals, respectively, to T-cells. K562/REP7β cells lack detectable B7-1 (data not shown) and provide a suitable negative control for experiments with K562/B7-1 transfected cells (i.e., K562 cells stably transfected with a pREP7β vector containing human B7-1 cDNA sequence). Surface B7-1 levels on K562/B7-1 transfected cells and B7-1•Fcγ$_1$-coated K562/REP7β cells were determined by immunostaining, and the mean fluorescence intensities were 550 nm and 450 nm, respectively. As shown in FIG. 4A, in the presence of suboptimal PHA concentrations (<0.5 μg/ml), B7-1•Fcγl-coated K562/REP7β cells, but not K562/REP7β, significantly enhance T-cell proliferation. The costimulatory effect was comparable to that achieved with K562/B7-1 transfected cells. The B7-1•Fcγ$_1$/pal-prot A-dependence of the observed costimulation was verified by showing that cells treated with a combination of (non-derivatized) protein A and B7-1•Fcγ$_1$ or with a combination of pal-prot A and control CD8•Fcγ$_1$, did not enhance T-cell proliferation. In the presence of higher PHA concentrations (>1 μg/ml), K562/REP7β cells also costimulate T-cell proliferation, although to a lesser extent than the B7-1 positive cells.

To further confirm the costimulatory function of cell-associated B7-1•Fcγ$_1$, proliferation assays were performed in which plate-bound anti-human CD3 mAb was substituted for PHA as a more physiological first signal. In this setting, in the presence of sub-optimal concentrations of anti-CD3 mAb (<10 µg/ml) cell-associated B7-1•Fcγ, costimulated even more effectively than native B7-1 expressed at equivalent levels on transfected cells, as shown in FIG. 4B. Again, CD8•Fcγ$_1$, used as a negative control Fc fusion protein, did not costimulate under the same conditions. Taken together, these results establish that B7-1•Fcγ$_1$, tethered to membranes via pal-prot A, effectively costimulates T-cell proliferation.

Effective depletion of accessory cells was documented in all T-cell preparations by demonstrating the lack of response to PMA or PHA in the absence of a source for costimulation. Points shown in FIGS. 4A and B are the means and SEs of triplicate samples. The data are representative of at least three independent experiments with similar results.

Figure 5:
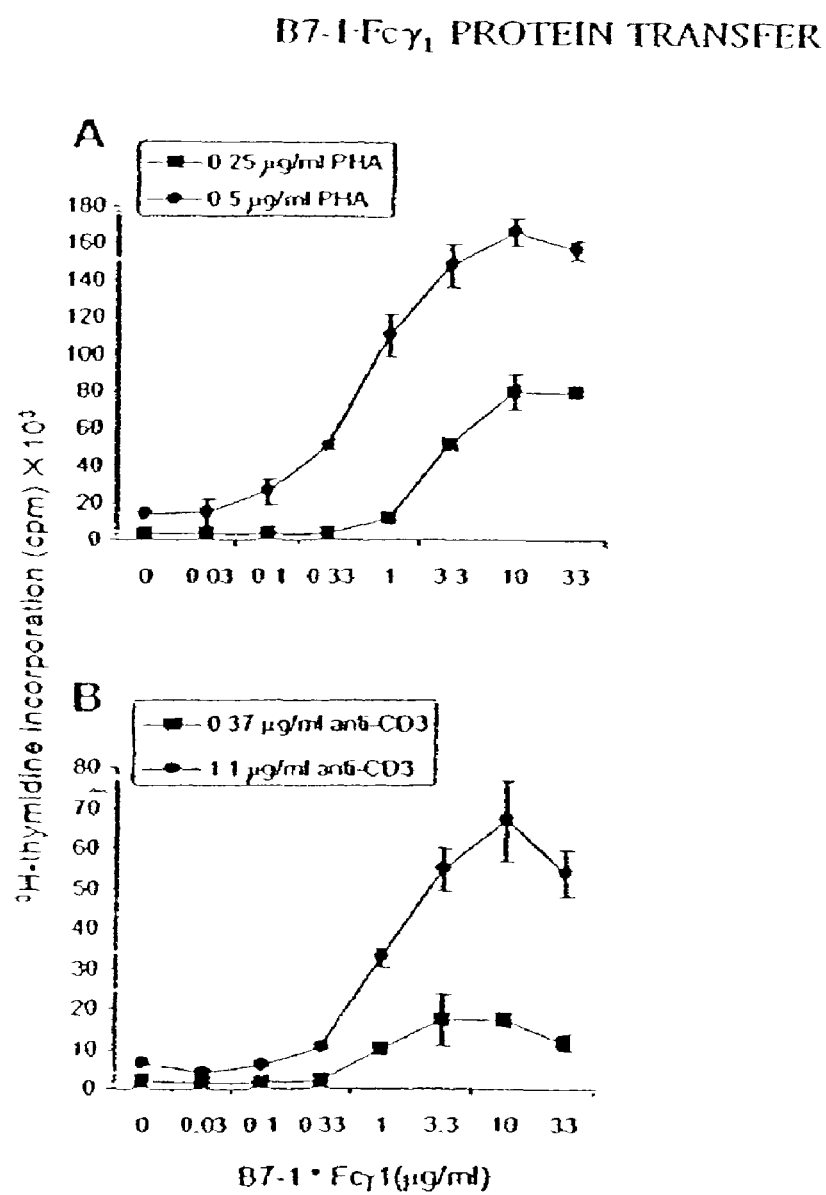
FIG. 5 demonstrates B7-1 threshold concentrations for T-cell proliferation using either PHA (FIG. 5A) or anti-CD3 mAb (FIG. 5B) as a first signal, as described in Example 1.

Concentration-Dependence of Cell-Associated B7-1•Fcγ$_1$§s Costimulatory Activity With an effective costimulator protein transfer method in hand, quantitative aspects of B7-1 costimulation were evaluated. To this end, T-cell proliferation assays were performed using K562/REP7β cells painted with variable concentrations of B7-1•Fcγ$_1$. The concentration dependence of B7-1•Fcγ$_1$-mediated costimulation could be readily demonstrated when a fixed suboptimal concentration of PHA (0.25 or 0.5 µg/ml) was used as a source of first signal, as shown in FIG. 5A. For example, in the presence of 0.5 µg/ml PHA, T-cell proliferation was observed once a threshold B7-1•Fcγ, concentration (0.1 µg/ml) was reached, and the level of proliferation continued to rise with increasing B7-1•Fcγ$_1$ concentrations until reaching a plateau at ~3.3 µg/ml. In the presence of a lower concentration of PHA (0.25 µg/ml), T-cell proliferation was observed when a higher threshold B7-1 concentration (1 µg/ml) was reached, indicating that costimulator thresholds can be modulated by the strength of the first signal.

Similar results were obtained when anti-human CD3 mAb was used as a source of first signal instead of PHA, as shown in FIG. 5B. Again, in the presence of a fixed suboptimal concentration of plate-bound anti-CD3 mAb (0.37 or 1.1 µg/ml), costimulation was observed only after a threshold B7-1•Fcγ$_1$ concentration was reached, and a further dose-dependent increase in proliferation was also seen. Hence, in the presence of a suboptimal first signal (whether PHA or anti-CD3 mAb), a threshold B7 level is required for T-cells to proliferate and the extent of T-cell proliferation is dictated by the costimulator level.

Figure 6:
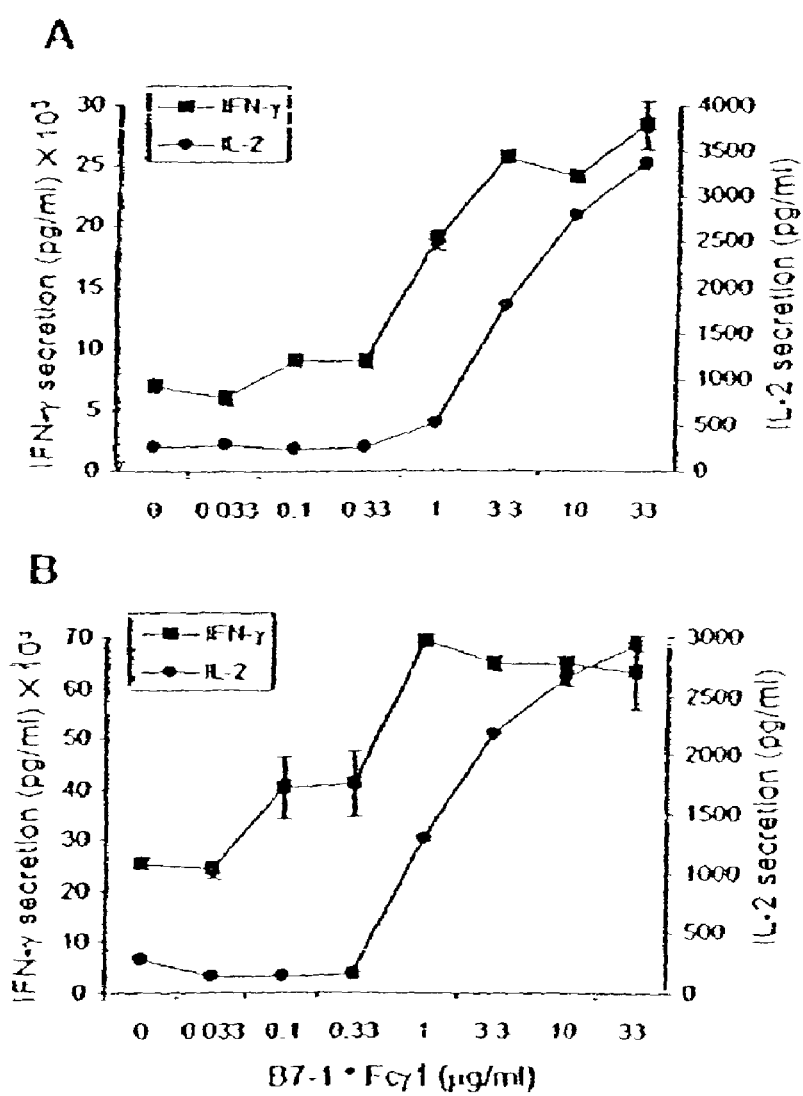
FIG. 6 provides a comparison of B7 concentration thresholds for IFN-$\gamma$ versus IL-2 production using either PHA (FIG. 6A) or anti-CD3 mAb (FIG. 6B) as a first signal, as described in Example 1.

ELISA Measurement of Secreted Cytokines and Determination of a Hierarchy of B7-1 Costimulator Thresholds for Distinct Cytokine Responses A total of $10^6$ T-cells was incubated with $5\times10^5$ processed K562/REP7β cells (B7-1•Fcγ$_1$ positive or negative) in 48-well plates using either plate-bound HIT3a or PHA as a source of first signal. Supernatants were collected after 48 h, and ELISAs for human IFN-γ and IL-2 were performed using a commercial ELISA kit according to manufacturer's protocol (Genzyme, Cambridge, Mass.). More specifically, ELISA was used to measure T-cell cytokine secretion in response to varying painted B7-1•Fcγ$_1$ concentrations and fixed suboptimal primary stimulus concentrations. At a fixed PHA dose, the B7-1•Fcγ, concentrations eliciting minimal and maximal cytokine responses differed for IFN-γ and IL-2 with the general hierarchy being IFN-γ<IL-2, as shown in FIG. 6A. A similar hierarchy for the cytokine responses was observed when anti-CD3 mAb (3.3 µg/ml) was used as a source of first signal as shown in FIG. 6B. For instance, at a B7-1•Fcγ$_1$ concentration of 0.33 µg/ml, IFN-γ output was 60% of the maximal response, whereas IL-2 output showed no increase above basal levels (FIG. 6B). This observed IFN-γ>IL-2 hierarchy for B7-1 costimulator thresholds matches the order described for TCR activation thresholds. Having documented that B7-1 levels can modulate the extent of T-cell proliferative responses, it was then determined that B7-1 levels can also dictate the quality of immune responses by altering the ratios of cytokines produced by activated T-cells.

Analysis of Intracellular Cytokine Production and Evaluation of Evidence for Hierarchical Costimulator Thresholds for Cytokine Responses at the Single-Cell Level To substantiate the ELISA findings with bulk T-cell populations, multiparameter flow cytometric analyses were performed to assess intracellular IFN-γ and IL-2 levels within individual cells. A total of 106 T-cells was incubated with $5\times10^5$ B7-1•Fcγ$_1$-coated K562/REP7β cells in 48-well plates for 48 h. Again, either plate-bound HIT3a or PHA was used as a source of first signal. Monesin (Sigma) was added to a final concentration of 3 µM, and the mixture was incubated for an additional 6 h to accumulate cytokine within the cells. Cells were then collected, fixed by incubating them in 100 µl of fixation solution [4% paraformaldehyde/PBS (pH 7.4)] on ice for 20 min. and then washed twice with staining buffer (0.1% saponin/1% heat-inactivated FCS/0.1% sodium azide/Dulbecco's PBS). Immunostaining for intracellular cytokines was performed by incubating the cells on ice for 1 h with 100 µl of the staining buffer containing 0.5 µg of FITC-anti-IFN-γ and 0.5 µg of PE-anti-IL-2 Abs (PharMingen). Cells were subsequently washed once with staining buffer without saponin. T-cells were gated using forward light scatter/side light scatter parameters, and $2\text{-}5\times10^4$ cells were analyzed in each run.

Figure 7:
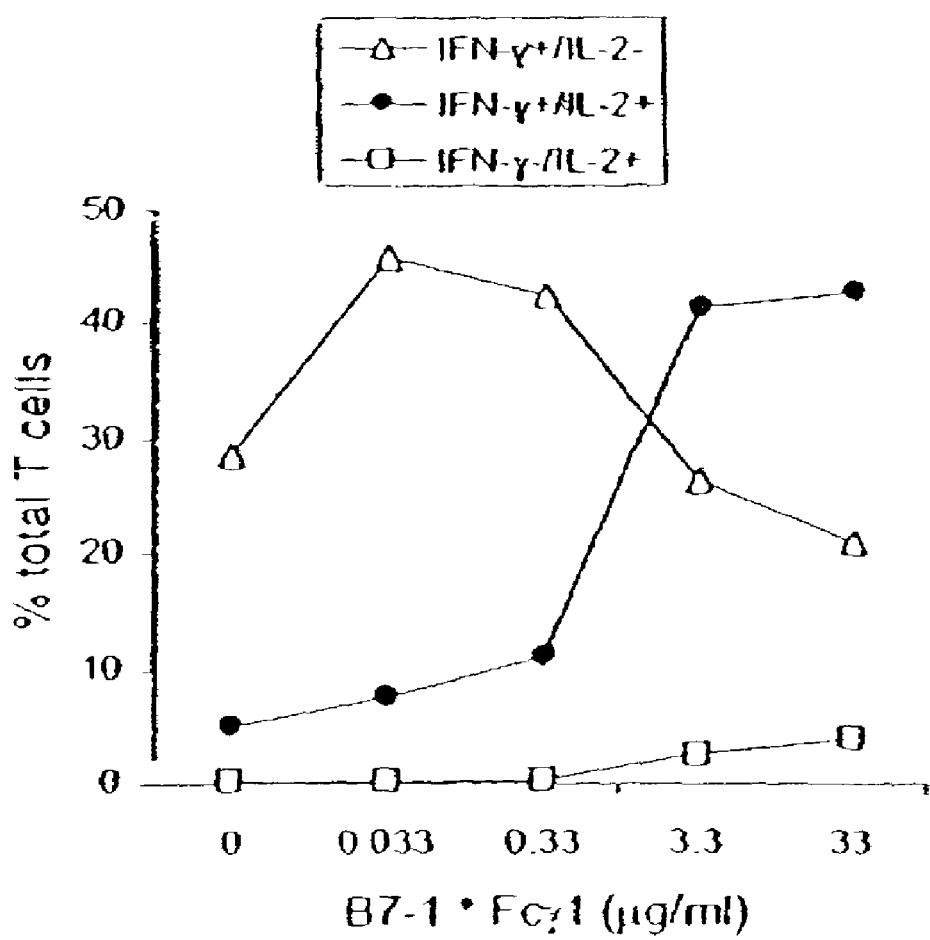
FIG. 7 provides comparative single-cell analyses of B7-1 concentration thresholds for IFN-$\gamma$ versus IL-2, as described in Example 1.

At low B7-1•Fcγ, concentrations, the T-cell response was dominated by IFN-γ-only producers; however, at higher B7-1•Fcγ$_1$ concentrations, substantial numbers of IFN-γ and IL-2 double producers emerged (FIG. 7). Relatively few IL-2 only producers were observed, even at the highest B7-1•Fcγ$_1$ concentrations. These findings are consistent with the bulk T-cell cytokine response data, showing that an IFN-β response requires less B7-1 costimulators than does an IL-2 response.

Example 2

The effect of temperature on membrane-incorporated protein A was studied; the transferred protein must remain cell-bound in vivo in order to prime T-cells, which requires stable engagement of costimulators for at least several hours. It was determined that the reaction temperature at which a lipidated protein is transferred to the cell membrane has a major impact on long-term retention of the protein on the membrane. Protein transfer reactions were performed at 4° C., 25° C. or 37° C.; palmitated protein A was transferred onto K562 cells. An hB7-1•Fc was $^{125}$I-labeled and transferred to the protein A-coated cells in the manner described in Example 1. To prevent interference of endocytosis likely to occur at temperatures above 4° C., the cells were treated with the metabolic inhibitors sodium azide and 2-deoxyglucose prior to the transfer reaction.

Figure 8:
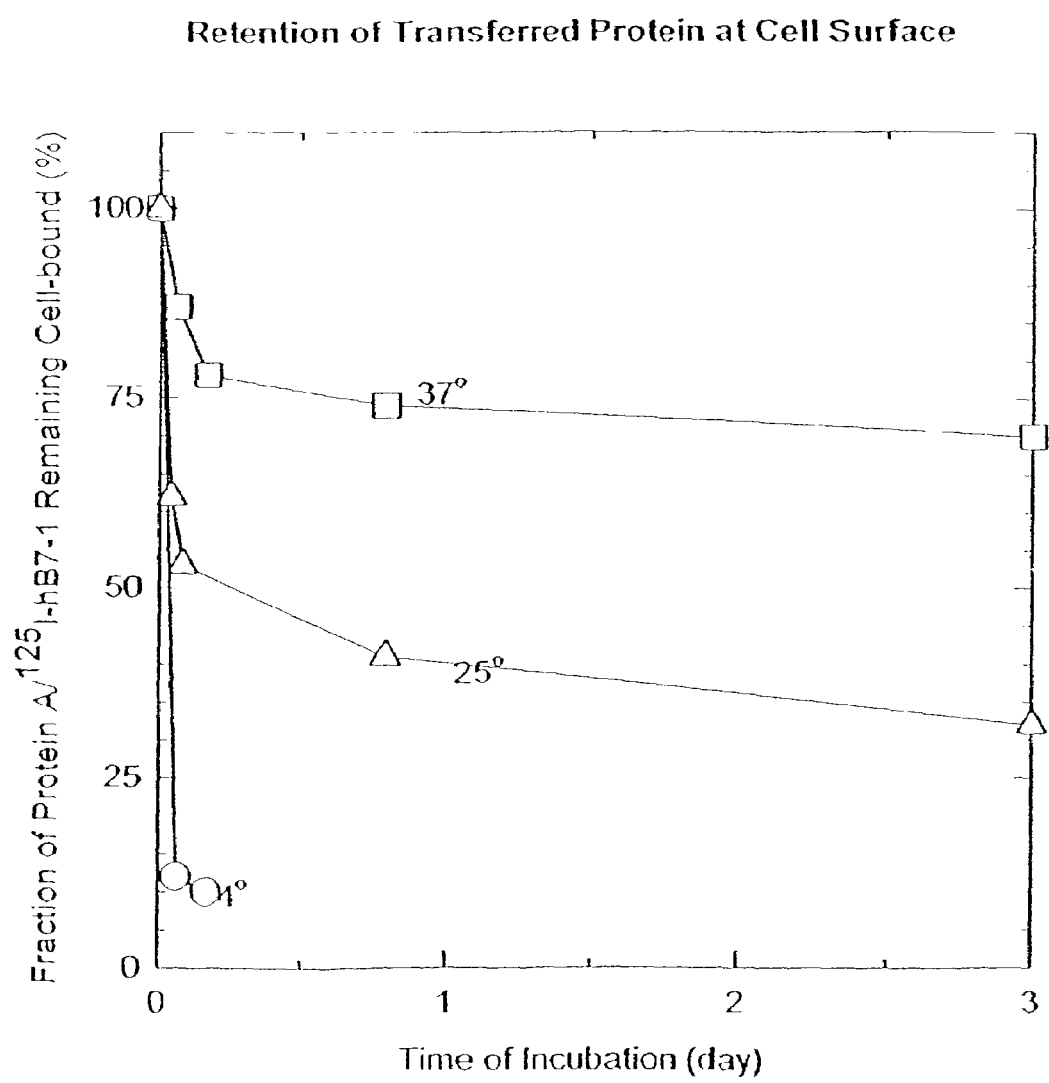
FIG. 8 shows the effect of reaction temperature during protein transfer on the stability of transferred protein, as described in Example 2.

To determine the long-term retention of the transferred protein on the cell membrane, the cells were thoroughly washed to remove unincorporated proteins, and subsequently incubated in suspension for up to three days at 37° C. in DMEM medium containing 10% fetal calf serum. At several intervals, aliquots of the suspension were taken and cells were pelleted. The amount of radioactive label remaining in the cell pellet was compared to the total amount of radioactive counts in the aliquot. The ratio between the two was calculated as the relative portion of the transferred protein still retained on the cell membrane. As depicted in FIG. 8, there is a direct relationship between a higher protein transfer reaction temperature and a better long-term retention rate. More importantly, by raising the transfer temperature from 4° C. to 37° C., the transferred proteins can remain membrane-bound at the physiological temperature of 37° C. for three days without significant loss (after the initial six hours).

Example 3

Figure 9:
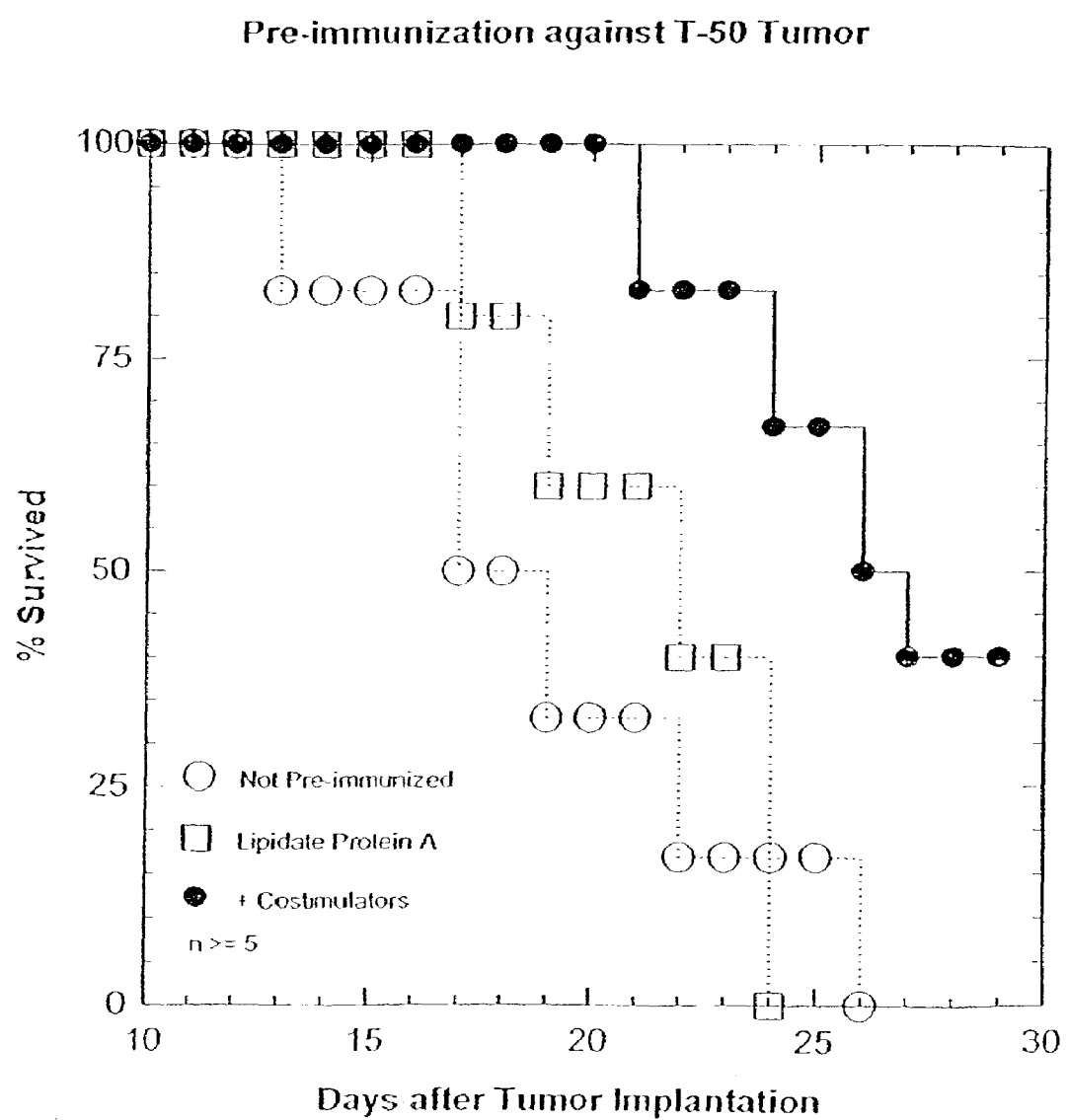
FIG. 9 demonstrates the efficacy of the present cancer vaccines in protecting a patient against a post-immunization tumor challenge, as described in Example 3.

C3H/HeN mice, purchased from Harlen (USA), Indianapolis, were immunized with a cell vaccine generated from the T-50 cell line, obtained from Avranham Hochberg, Hadassah University Hospital. The vaccine was prepared following the procedure generally outlined in Example 1, using palmitated protein A and nB7-1ωFc, m4=1 BBL•Fc, and hCD40L•Fc fusion proteins. Basically, the cells were coated with the lipidated protein A at 37° C. at a ratio of 40 μg protein A per $40 \times 10^6$ cells. The cells were then incubated at 4° C. with an equal mixture of the three fusion proteins at a ratio of 20 μg total protein per $4 \times 10^7$ cells. The cell vaccine was injected into the mice subcutaneously at a dose of $10^6$ cells per injection. The injections were given once a week and continued for three weeks. One week after the last injection, the animals were challenged with $10^6$ wild-type T-50 tumor cells, injected intradermally on the rear flank. As FIG. 9 shows, the cell vaccine improved the survival rate of the immunized animals. In FIG. 9: open circle, an untreated control group (n=6); square, another control group that received a control vaccine generated by protein A transfer (n=5); closed circle, the test group that received a cell vaccine generated by protein transfer with immune costimulatory proteins B7-1, 4-1BBL, and CD40L in complex with protein A (n=6).

Example 4

Figure 10:
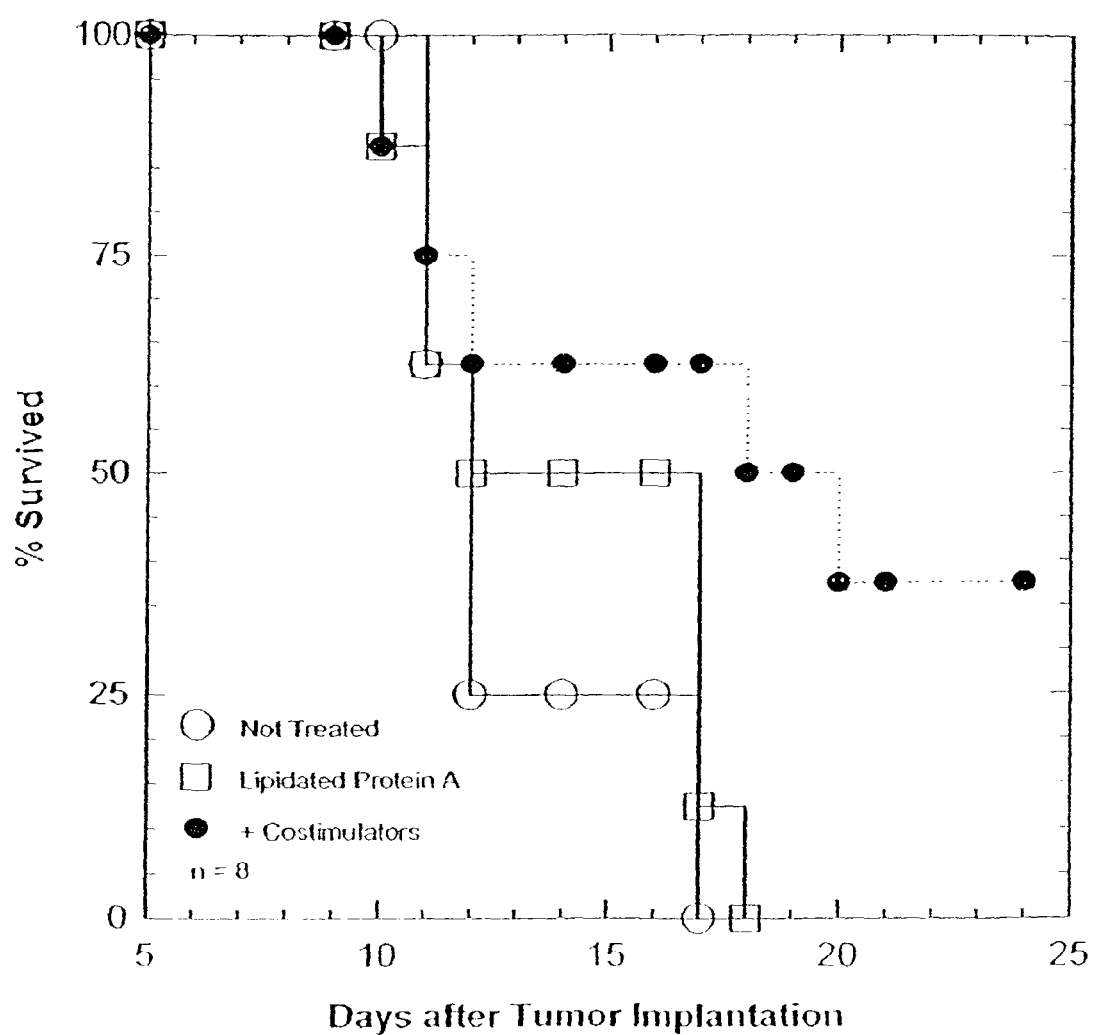
FIG. 10 demonstrates the efficacy of the present cancer vaccines in treating a pre-existing tumor, as described in Example 4.

DBA/2J mice were purchased from The Jackson Laboratory, Maine. The animals were inoculated intradermally with a lethal dose of L5178Y-R tumor cells and given subcutaneous injections of a cell vaccine as a treatment on days 5, 6, and 7 after the tumor inoculation. The same cell vaccine in Example 3 was used here, at a dose of 106 cells per injection. FIG. 10 shows that the cell vaccine improved the survival rate of the treated animals. In FIG. 10: open circle, an untreated control group (n=8); square, another control group that received a control vaccine generated by protein A transfer (n=8); closed circle, the test group that received the cell vaccine generated by protein transfer with the immune costimulatory fusion proteins in complex with lipidate protein A (n=8).

Example 5

A vaccine was formed with palmitated protein A and FasL•Fc, B7-1•Fc, 4-1BBL•Fc and CD40L•Fc fusion proteins by mixing them in vitro at three parts of lipidated protein A and one part of each of the fusion proteins. The protein mixture was then injected intratumorally at 4 μg of total protein per tumor site. The vaccine was subsequently injected directly into a tumor; the immune costimulatory proteins in the vaccine modified the immunogenic property of tumor cells in situ.

Figure 11:
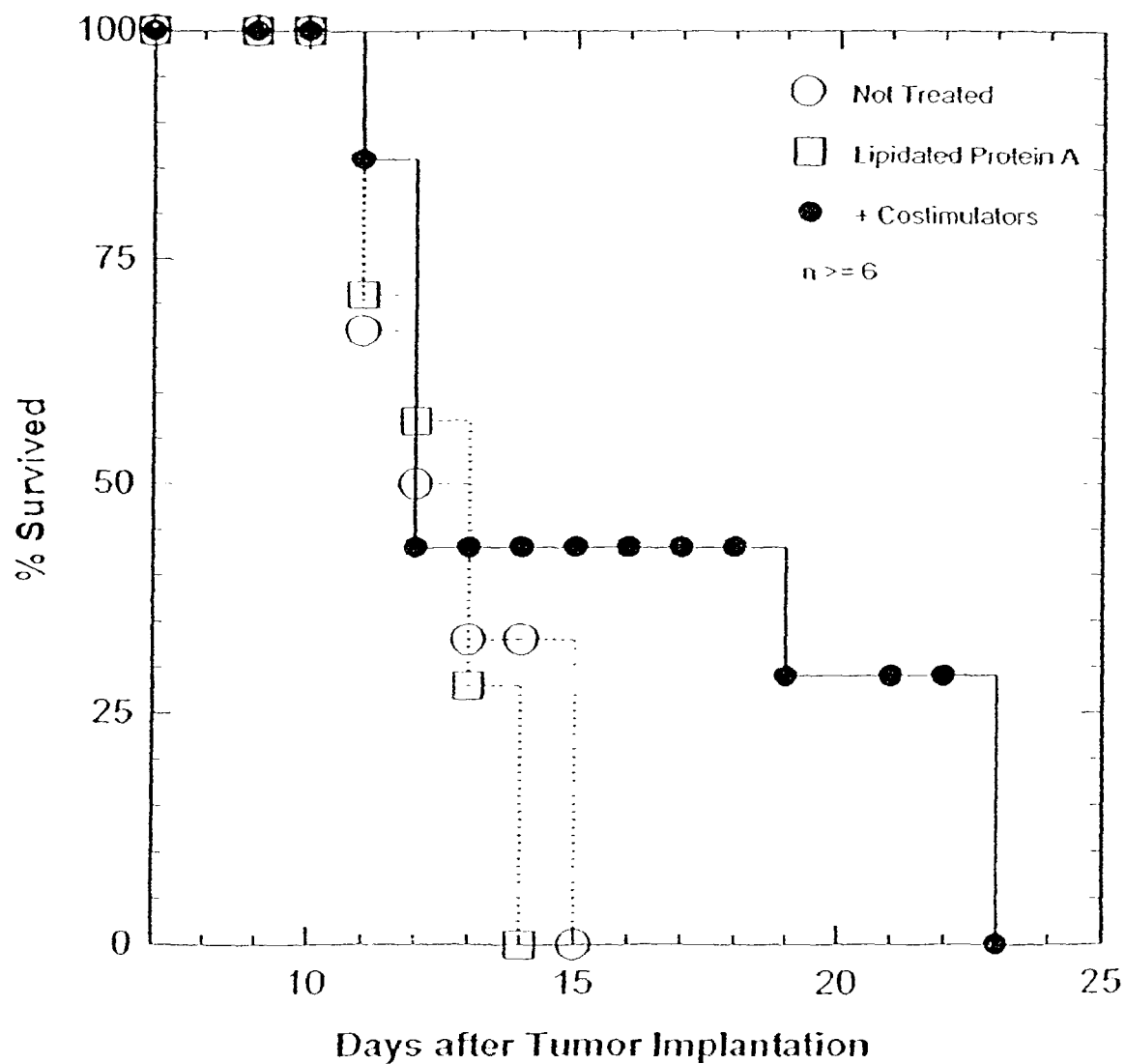
FIG. 11 demonstrates the efficacy of the present cancer vaccines by intratumoral injection of costimulators, as described in Example 5.

DBA mice were inoculated with a lethal dose of L5178Y-R tumor cells. As tumor mass grew to about 50 mm² in size, the cancer vaccine was injected directly into the tumor site. The vaccines were pre-assembled with palmitated protein A, which confers the ability to anchor costimulators on the tumor cells in situ according to the present methods. As shown in FIG. 11, the survival of the mice treated with the indirectly lipidated costimulators was significantly prolonged. In FIG. 11: open circle, an untreated control group (n=6); square, another control group that were injected with lipidated protein A alone (n=7); closed circle, the test group that were injected with the immune costimulatory fusion proteins in complex with lipidate protein A (n=7).

Example 6

To generate a fusion protein for FasL, a coding sequence for a human $Fc\gamma_1$ domain, obtained from ATCC, was fused at the N-terminus of the coding sequence for the extracellular domain of FasL following the fusion strategy reported in *Immunity,* 5:163, 1996. The purified fusion protein was fully functional, as determined by a standard killing assay when loaded on protein A-coated cells. FasL is a cell surface protein that binds to another protein, Fas, found on the surface of other cells, for example, activated T-cells. When FasL binds to Fas, the cells expressing Fas undergo apoptosis. Significantly, the FasL•Fc fusion protein, after being transferred onto the cell surface through the lipidated protein A, retained its apoptotic activity.

More specifically to determine whether the Fc-hFasL fusion protein was functional after anchoring onto cell surfaces, a standard JAM assay is performed. The effector cells were CHO cells that were painted with palmitated protein A (pal-prot A) and subsequently with Fc fusion protein. The target cells were Jurkat cells that constitutively express Fas and thus are susceptible to Fas/FasL-mediated apoptosis. A standard JAM assay was performed, according to the protocol described by P. Matzinger (*J. Immunol. Methods,* 145:185-192,1991). Briefly, $2 \times 10^4$ 3H-thymidine-labeled target Jurkat cells were co-incubated with $2 \times 10^5$ CHO cells (from ATCC) that were pre-coated with pal-prot A as previously described in Example 1, and subsequently painted with 30 μg/ml of Fc-hFasL fusion protein or control fusion protein. The cells were co-cultured in 200 μl of RPMI-10 in a 96-well plate for 18 hours at 37° C. in a humidified incubator at 5% $CO_2$. To harvest the JAM test, the cells and their medium were aspirated onto fiber glass filters using a harvester (as used in Example 1 for the proliferation assays). % specific killing was calculated as follows: (S−E)/S×100, where S=spontaneous release without effector cell, E=experimental release in the presence of effector cells.

Figure 12:
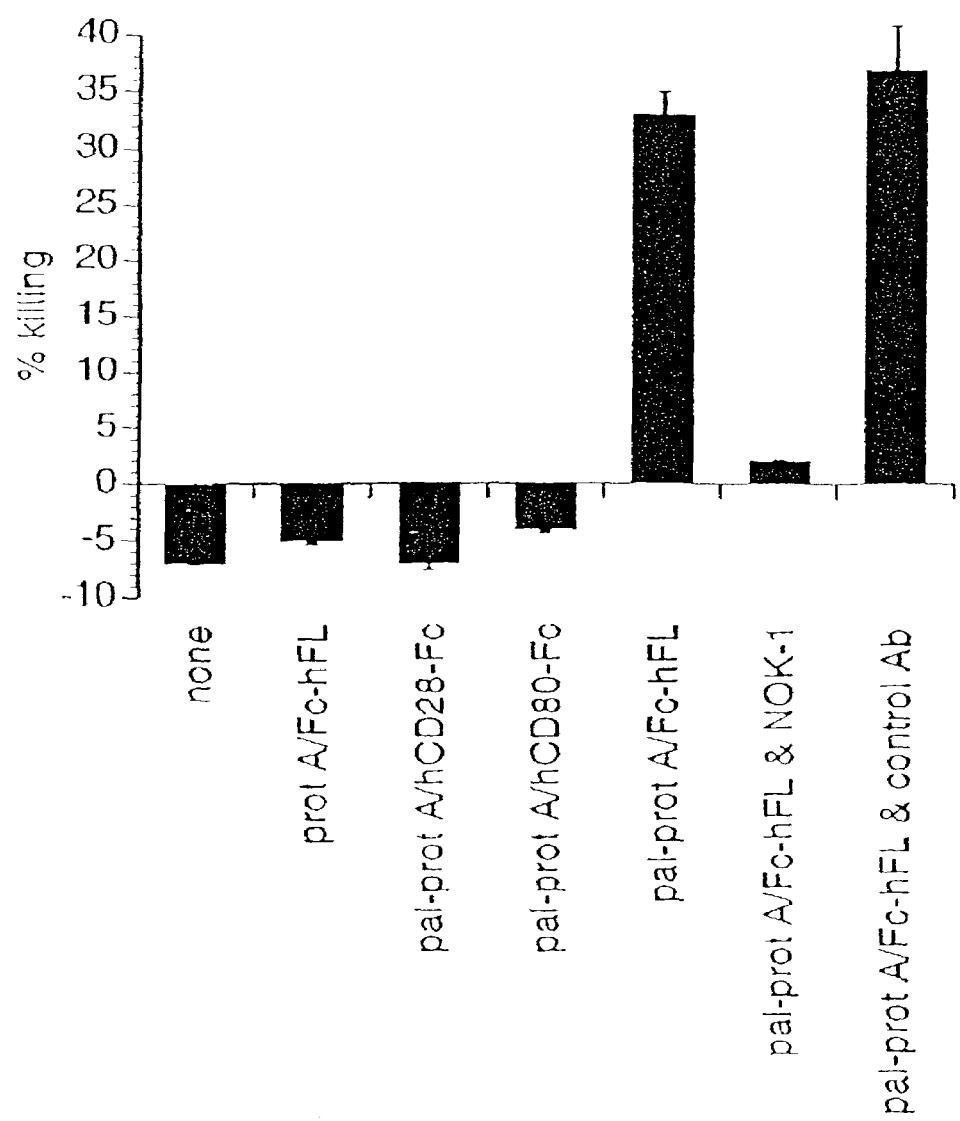
FIG. 12 shows the results of the JAM assay, as described in Example 6.

The results are summarized in FIG. 12. When CHO cells that were painted with pal-prot A and Fc-hFasL were used as effector cells, significant killing was observed. As negative controls, when CHO cells were painted with pal-prot A and control Fc fusion protein (hCD80-Fc or hCD28-Fc), no specific killing was observed. The surface anchorage-dependence of Fc-hFasL was demonstrated by the negative control where the CHO cells were painted with unpalmitated protein A and Fc-FasL. The specificity of the killing was demonstrated by complete blockade of the killing by FasL neutralizing mAb NOK-1, whereas the control Ab did not block the killing.

In summary, these results demonstrate that Fc-hFasL, after being transferred onto cell surface through pal-prot A, retains its function to elicit apoptosis in Fas-positive Jurkat cells.

The above examples demonstrate the efficacy of the present methods. Through the use of lipidated proteins, fusion proteins can be transferred to cells both ex vivo and in situ. Significantly, these fusion proteins retain their immunoregulatory function after transfer. The examples demonstrate this retained function against post-imitation challenge and against pre-existing tumors. The methods were demonstrated as being effective both in vivo and in vitro.

Example 7

The following example demonstrates that murine splenic T cells painted with a B7-1●Fc$_{\gamma 1}$:palmitated-protein A conjugate have enhanced proliferative potential in response to primary anti-CD3 mAb triggering of their TCR.

Membrane Incorporation of B7-1●Fc$_{\gamma 1}$:Palmitated-Protein A and Fc$_{\gamma 1}$●4-1BBL:Palmitated-Protein A Conjugates We applied the above methods to T cells for the first time in order to produce pure and uniform B7-1$^+$ or 4-1BBL$^+$ T cells ex vivo. Murine CD4$^+$ or CD8$^+$ T cells were purified from the spleens of DBA/2J mice (Jackson Laboratory, Bar Harbor, Me.) and painted separately with palmitated-protein A and Fc$_{\gamma 1}$-derivatized B7-1, 4-1BBL, and CD28 proteins (B7-1●108 Fc$_{\gamma 1}$, Fc$_{\gamma 1}$●4-1BBL, and CD28●Fc$_{\gamma 1}$) in two sequential steps. Specifically, the purified cells were mixed with palmitated-protein A at 30 μg per 10$^6$ cells per ml in DMEM, at 37° C. for 1 h. The cells were washed and mixed again with B7-1●Fc$_{\gamma 1}$, Fc$_{\gamma 1}$●4-1BBL, or CD28●Fc$_{\gamma 1}$ (as negative control) at 30 μg per 10$^6$ cells per ml in DMEM, at 4° C. for 0.5 h. The preparation of palmitated-protein A is as described above. The production of B7-1●Fc$_{\gamma 1}$, Fc$_{\gamma 1}$●4-1BBL, and CD28●Fc$_{\gamma 1}$ has also been described previously (Zheng, et al. Cancer Res., 61:8127 (2001)).

The B7-1●Fc$_{\gamma 1}$-painted T cells were analyzed by flow cytometry following immunostaining with the rat anti-mouse B7-1 mAb IG10 as primary Ab, and FITC-labeled goat anti-rat conjugates as second Ab (BD Pharmingen, San Diego, Calif.). Negative control rat IgG$_{2a}$ isotype-control mAb was also obtained from BD Pharmingen. Of note, the rat Ab do not bind to protein A. Cells were analyzed on a FACSAN (Becton Dckinson, Mountain View, Calif.), and events were gated on live cells.

Figure 13A:
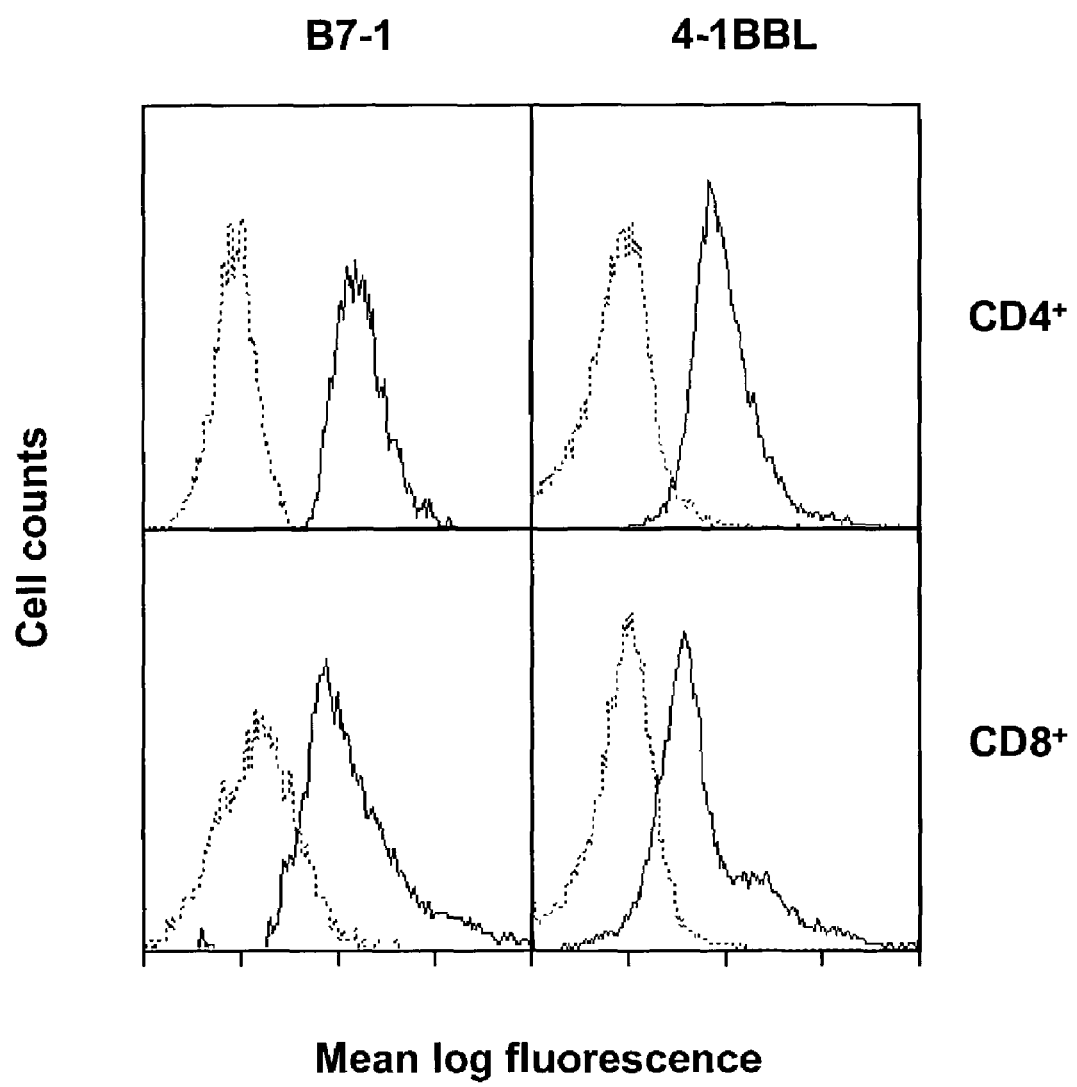
FIG. 13, including 13A and 13B, demonstrates the efficacy of painting both $CD4^+$ and $CD8^+$ murine T cells with two different costimulators, and the enhanced T cell proliferative potential of these costimulator-painted T cells, according to the methods of Example 7.

As shown in FIG. 13A (left panels), significant B7-1-positivity was evident on the treated cells, whether CD4$^+$ or CD8$^+$. In contrast, B7-1 epitopes were undetectable on untreated splenic T cells, as well on those cells exposed to the B7-1●Fc$_{\gamma 1}$ fusion protein in the absence of palmitated-protein A or in the presence of native (non-palmitated) protein A (data not shown).

To establish the generality of this T cell costimulator painting method, Fc$_{\gamma 1}$●4-1BBL was substituted for B7-1●Fc$_{\gamma 1}$ in the above experimental design. 4-1BBL-painted T cells were generated with biotin-labeled-Fc$_{\gamma 1}$●4-1BBL, which was subsequently detected using avidin-FITC conjugates as fluorescent tags (BD Pharmingen, San Diego, Calif.). As shown in FIG. 13A (right panels), significant levels of 4-1BB ligand epitopes were detectable on both CD4$^+$ and CD8$^+$ T cells following the painting step.

Enhanced Proliferation of Murine Splenic T Cells painted with B7-1●Fc$_{\gamma 1}$:Palmitated-Protein A and Fc$_{\gamma 1}$●4-1BBL:Palmitated-Protein A Conjugates Purified murine CD4$^+$ or CD8$^+$ splenic T cells were prepared from the spleens of DBA/2J purchased from the Jackson Laboratory (Bar Harbor, Me.). The cells were painted ex vivo with either B7-1●Fc$_{\gamma 1}$:Palmitated-Protein A or Fc$_{\gamma 1}$●4-1BBL:palmitated-protein A conjugates, and then plated in wells containing a sub-optimal amount of plate-bound rat anti-mouse CD3 mAb (in the absence of accessory cells). Specifically, B7-1- or 4-1BBL-painted murine T cells were plated in 96-well flat-bottomed plates that were pre-coated with dialyzed rat anti-mouse CD3 mAb (TK3; Serotec Ltd, Oxford, UK) at 1 μg per ml, 37° C. for 3 h. The cells were seeded at 10$^5$ cells per well, in RPMI 1164 medium supplemented with 10% fetal calf serum, 15 mM HEPES, and 50 mM β-ME. At 48 h, $^3$H-thymidine was added to the culture, at 1 μCi per well, and the cells were harvested at 64 h. $^3$H-thymidine incorporation was analyzed with a β-Counter.

Figure 13B:
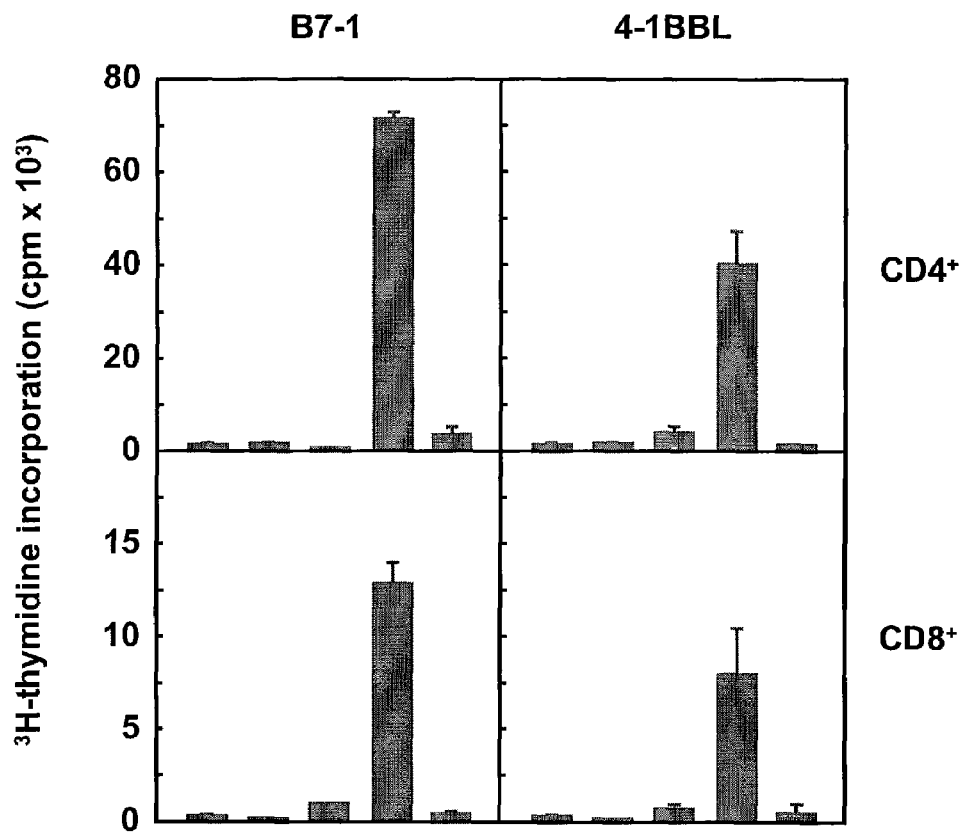

As shown in FIG. 13B, the various costimulator-painted T cells, including B7-1- and 4-1BBL-painted CD4$^+$ and CD8$^+$ T cells, all proliferated vigorously (FIG. 2). In contrast, relatively little proliferation was seen in the various controls, including non-painted T cells treated with anti-CD3 mAb, T cells painted with Fc$_{\gamma 1}$-derivatized murine CD28 (a non-costimulator control), T cells treated with native (non-lipidated) protein A in place of palmitated-protein A, and costimulator-painted T cells in the absence of an anti-CD3 mAb stimulus.

Figure 14A:
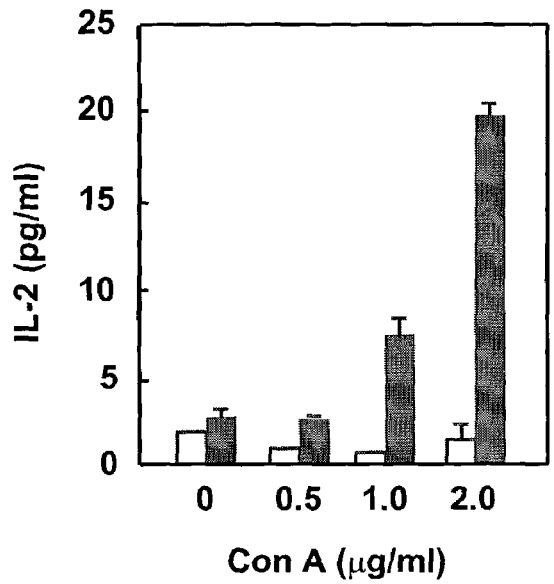
FIG. 14, including 14A and 14B, demonstrates the enhanced proliferative potential of a murine T cell line (EL-4) and purified human T cells after costimulator painting, according to the methods of Example 7.

Enhanced IL-2 Production by Murine EL-4 T Cells Painted with B7-1●Fc$_{\gamma 1}$:Palmitated-Protein A Conjugates As further proof that contaminant APC in the purified T cell preparations are not responsible for the observed proliferative response, the homogeneous EL-4 T lymphoma line was tested. Since EL-4 cells proliferate spontaneously in culture, IL-2 secretion was used as an alternative readout for stimulation. EL-4 cells were painted with B7-1●Fc$_{\gamma 1}$:palmitated-protein A conjugates and plated in wells of 96-well flat-bottomed plates containing decreasing amounts of either plate-bound anti-CD3 mAb (not shown) or concanavalin A as mitogen. Conditioned medium was taken 12 h later and analyzed for IL-2 with the use of a commercial ELISA kit (R&D Systems, Minneapolis, Minn.) as per the manufacturer's protocols. As shown in FIG. 14A, B7-1-painted EL-4 cells secreted more IL-2, as compared to non-painted control cells under these sub-optimal mitogen stimulation conditions.

Enhanced Proliferation of Purified Human T Cells painted with B7-1●Fc$_{\gamma 1}$:Palmitated-Protein A Conjugates In order to extend the findings beyond murine cells, human CD4$^+$ T cells were prepared from the peripheral blood of healthy donors. All T cells were purified by magnetic separation, as per the manufacturer's instructions (Miltenyi Biotec, Auburn, Calif.). These cells were painted with B7-1●Fc$_{\gamma 1}$:palmitated-protein A conjugates and assayed for proliferation under sub-optimal anti-CD3 stimulation. Specifically, the plates were pre-coated with azide-free mouse anti-human CD3 mAb (HIT3A; BD Pharmingen) at 0.3 μg per ml.

Figure 14B:
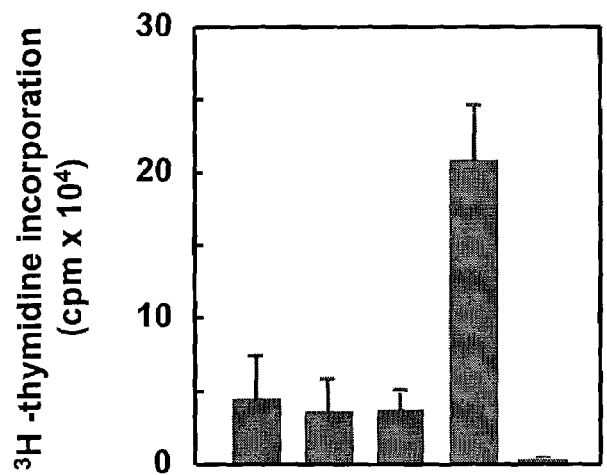

As shown in FIG. 14B, the B7-1-painted human CD4$^+$ T cells, like their murine counterparts, proliferated vigorously in an anti-CD3 mAb-dependent manner, whereas the non-painted or control-painted cells proliferated relatively little.

CD28-Dependence of the Enhanced Proliferation of B7-1-Painted Murine Splenic T Cells In order to verify that the costimulatory effect observed for B7-1-painted murine splenic CD4$^+$ T cells is indeed dependent upon binding to B7-1's cognate receptor on the same T cells, CD28, we evaluated the proliferative potential of splenic T cells purified from CD28$^{-/-}$ C57BL/6 knockout mice (purchased from the Jackson Laboratory, Bar Harbor, Me.), after costimulator painting. The cells were processed and assayed as described above, except that the CD28$^{-/-}$ CD4$^+$ T cells were pulsed with $^3$H-thymidine at 12 h and harvested at 24 h.

Figure 15:
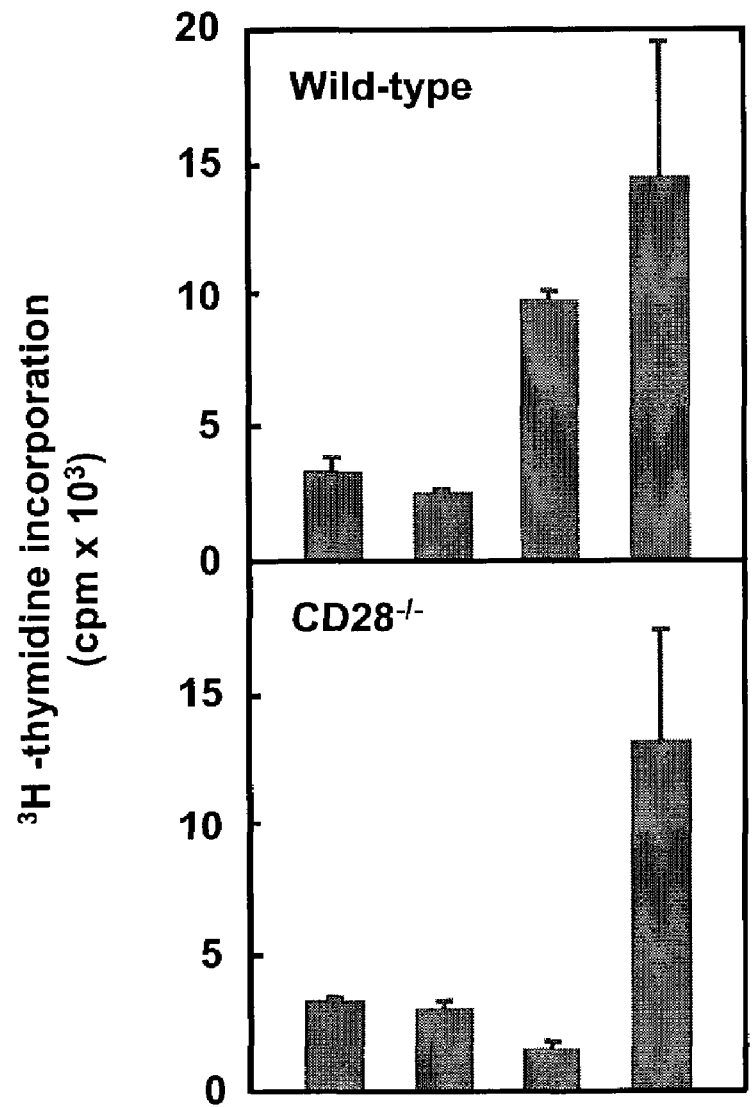
FIG. 15 documents the CD28-dependence of the enhanced proliferation observed for T cells painted with the B7-1 costimulator, according to the methods of Example 7.

As shown in FIG. 15, the B7-1-painted, CD28$^{-/-}$ knockout splenic CD4$^+$ T cells failed to proliferate, as compared to the robust proliferation of wild-type CD28-bearing cells. Significantly, the viability of the CD28$^{-/-}$ knockout splenic T cells was verified, by showing that they proliferated well after being painted with a second costimulator, 4-1BBL.

Example 8

The following example demonstrates that costimulator-painted T cells exhibit an enhanced proliferative response to a physiologic antigenic stimulus.

Figure 16A:
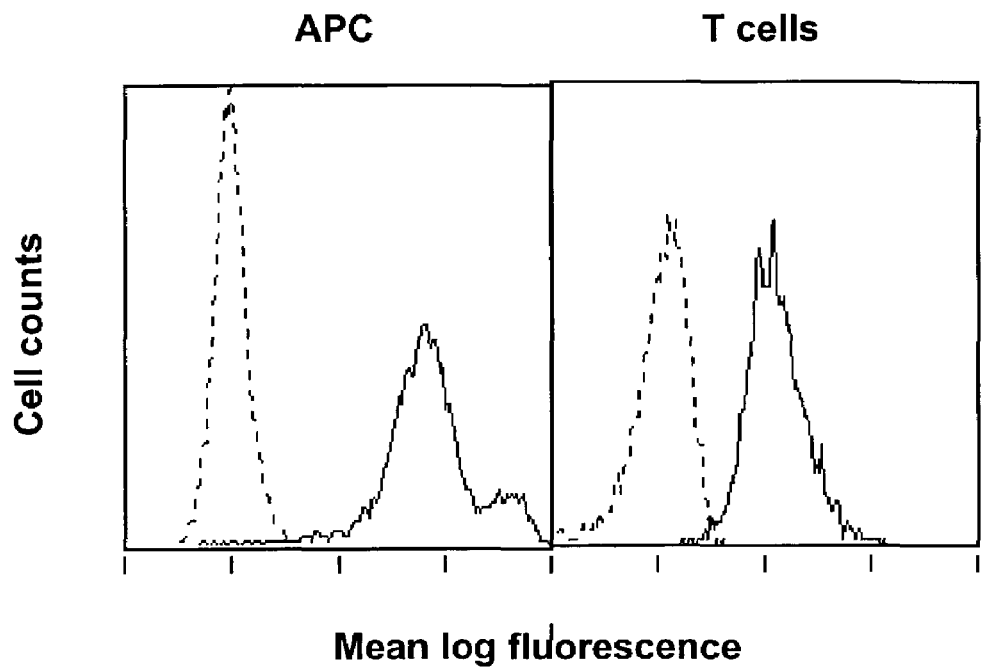
FIG. 16, including 16A and 16B, demonstrates that costimulator painting enhances the proliferative response of TCR-transgenic T cells to their specific cognate peptide antigen, according to the methods of Example 8.

Membrane Incorporation of B7-1●Fc$_\gamma$1:Palmitated-Protein A Conjugates on to the surfaces of DO11.10 TCR-transgenic T cells DO11.10 TCR-transgenic T cells, with OVA$_{323-339}$ peptide antigen specificity, generally depend on costimulator signaling from accessory cells for their proliferative response. We determined whether costimulator painting of these TCR-transgenic T cells can bypass this dependence on accessory cells for intercellular trans costimulation. To this end, we separately painted purified splenic T cells and the syngeneic APC cell line, PRO-IA$^d$, with B7-1●Fc$_{\gamma 1}$:palmitated-protein A conjugates, as described above. As shown in FIG. 16A, both cell populations exhibited substantial levels of B7-1 epitopes after this procedure.

Figure 16B:
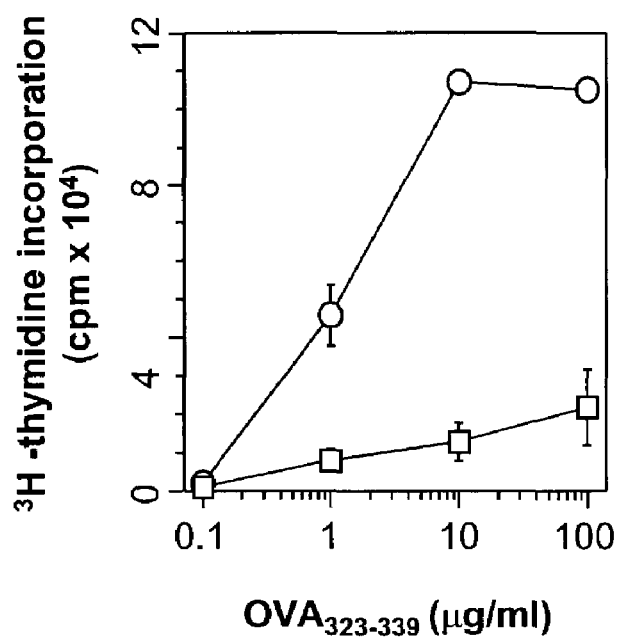

Enhanced Proliferation of DO11.10 TCR-Transgenic T Cells Painted with B7-1●Fc$_{\gamma 1}$:Palmitated-Protein A Conjugates in Response to Specific Cognate Antigen The proliferative response of B7-1-painted DO11.10 TCR-transgenic T cells (co-cultured with native PRO-IA$^d$ cells) to increasing concentrations of the OVA$_{323-339}$ peptide antigen was compared to non-painted T cells from the same source (co-cultured with PRO-IA$^d$ cells painted with B7-1●Fc$_{\gamma 1}$: palmitated-protein A conjugates). Equal numbers of T cells were present in both cultures. As shown in FIG. 16B, antigen-driven proliferation was markedly enhanced when B7-1 was expressed directly on the T cells, as opposed to the accessory cells.

Example 9

The following example demonstrates that auto-costimulation contributes significantly to the enhanced proliferation observed in cultures of costimulator-painted T cells.

Figure 17A:
FIG. 17, including 17A, 17B and 17C, demonstrates via cell-mixing experiments (that employ mitomycin C-inhibited cells) that auto-costimulation is a major contributor to the enhanced proliferation of costimulator-painted T cells, according to the methods of Example 9.
Figure 17A:
Figure 17A:
Figure 17A:
Figure 17A:
Figure 17A:

Distinguishing Between C is Auto-Costimulation and Trans Intercellular Costimulation: Cell Mixing Experiment with Mitomycin C inhibition Within a homogeneous population of costimulator-painted, costimulator receptor-bearing T cells, there are two possible modes of costimulation: trans intercellular costimulation and cis auto-costimulation. To quantitatively compare the two, we devised an experimental strategy based upon cell mixing, as depicted in FIG. 17A. A preparation of murine splenic CD4$^+$ T cells was divided into two: one-half was treated with mitomycin C to render them incapable of proliferation, whereas the other half was untreated. In turn, one-half of each of the mitomycin-treated and untreated cell populations was painted with costimulator●Fc$_{\gamma 1}$:palmitated-protein A conjugates.

With these four subpopulations of variably treated cells in hand, we set up three different cell mixtures, designated A, B and C, each consisting of equal numbers of mitomycin C-inactivated and untreated active cells. Mixture A consisted of costimulator-painted, inactivated cells combined with non-painted, active cells. Proliferation in this mixture reflects only trans intercellular costimulation. By contrast, in mixture B, it is the active cells that are costimulator-painted, and thus, proliferation in this mixture can arise from both intercellular trans costimulation and cis-auto-costimulation. The level of cis auto-costimulation can be calculated by subtracting the proliferation in mixture B (trans+cis) from that in mixture A (cis only).

Figures 17B, 17C:
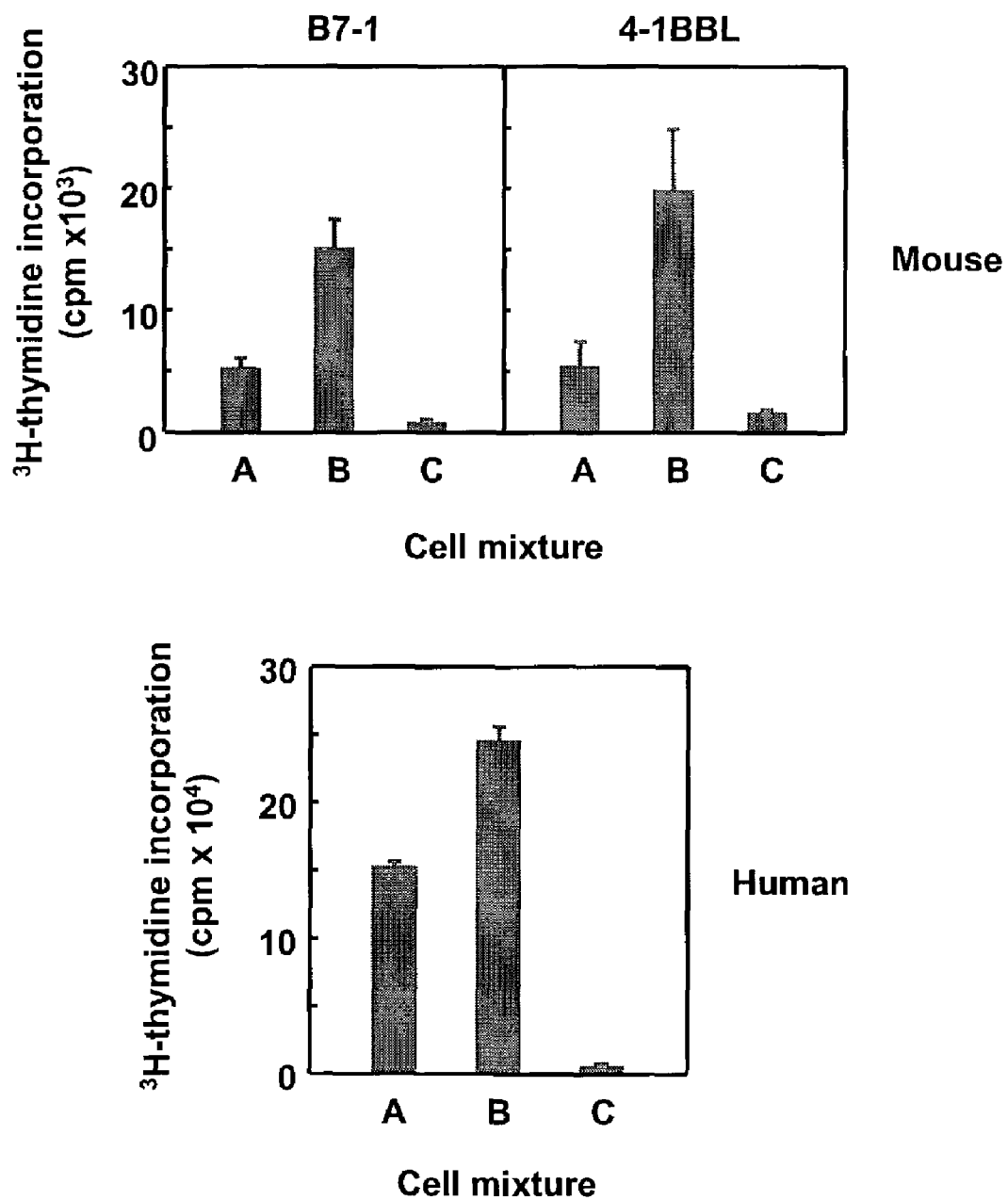

As shown in FIG. 17B, under conditions where a sub-optimal level of anti-CD3 mAb stimulation was employed, substantially more proliferation was observed in mixture B as compared to mixture A, for both B7-1- and 4-1BBL-painted murine CD4$^+$ T cells, pointing to substantial auto-costimulation for both costimulators. Mixture C, a control in which neither the mitomycin-treated nor the untreated cells were painted with costimulators, provided the background level of costimulation-independent level of proliferation in this culture system. As shown in FIG. 17C, a significant level of cis auto-costimulation was also observed in an analogous human CD4$^+$ T cell co-culture system.

Distinguishing Between C is Auto-Costimulation and Trans Intercellular Costimulation: Cell Mixing Experiment with CFSE-labeling To rule out the possibility that mitomycin C treatment somehow interferes with trans intercellular costimulation, we devised an alternative cell mixing protocol that avoided metabolic inhibitors altogether. For this second cell mixing experiment, we turned to CFSE labeling, which permits quantitation of proliferation by tracking decrements in CFSE fluorescence, which halves with each successive cell division. For the CFSE labeling, murine splenic CD4$^+$ T cells were suspended at 2.5×10$^6$ cells per ml in PBS containing 83 nM CFDASE (Molecular Probes, Eugene, Oreg.), at room temperature for 3 min. The reaction was terminated by adding fetal calf serum to 10%. The cells were washed twice before use in RPMI 1164 medium supplemented with 10% fetal calf serum, 15 mM HEPES, and 50 mM β-ME.

Figures 18A, 18B:
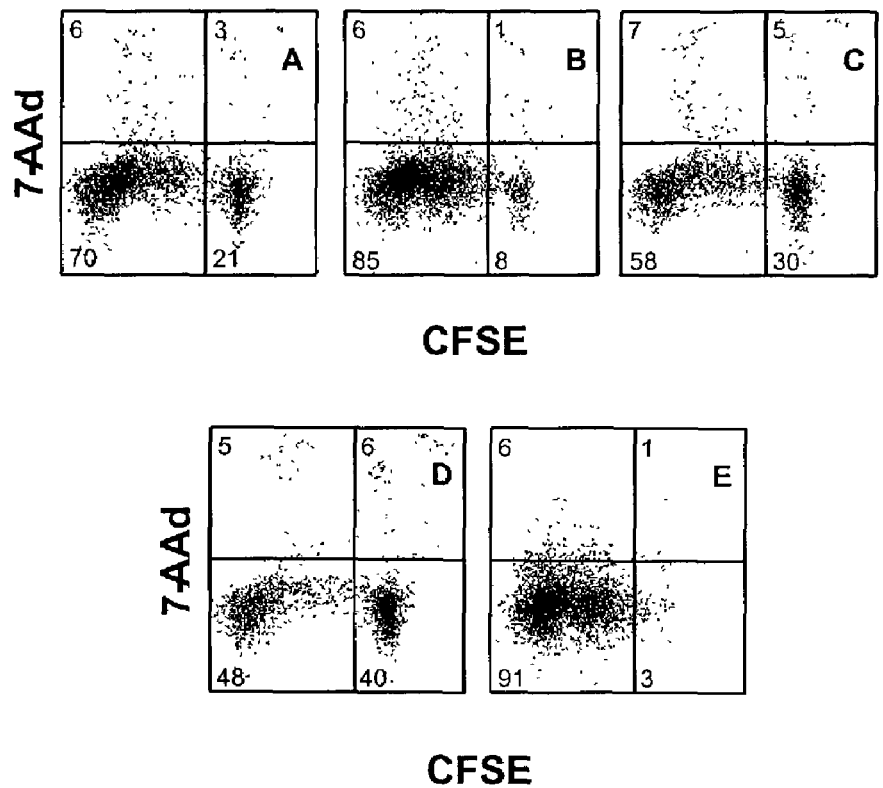
FIG. 18, including 18A and 18B, demonstrates via cell-mixing experiments (that employ CFSE-labeled cells) that that auto-costimulation is a major contributor to the enhanced proliferation of costimulator-painted T cells, according to the methods of Example 9.

The cell mixing scheme for the CFSE experiment is shown in FIG. 18A. In this case, mixture A consisted of CFSE-labeled cells combined with an equal number of costimulator-painted, unlabeled cells, plated in wells containing sub-optimal levels of anti-CD3 mAb. Thus any decrement in CFSE labeling in this mixture reflects trans intercellular costimulation. In mixture B, it is the CFSE-labeled cells that are costimulator-painted, and thus both trans intercellular costimulation and cis auto-costimulation are possible. Again, as in the case of the mitomycin C experiment, the difference in proliferation between mixtures B (trans+cis) and B (cis only) reflects the degree of cis auto-costimulation.

As shown in FIG. 18B, flow cytometry at 64 h revealed substantially fewer CFSE fluorescent cells in mixture B, as compared to A, pointing to a substantial level of cis auto-costimulation in that co-culture. As before, comparison of mixture A to mixture C (which lacked costimulator altogether), pointed to a significant level of trans intercellular costimulation as well. Thus, two independent cell mixing experiments pointed to significant auto-costimulation, in conjunction with basal trans intercellular costimulation.

Example 10

The following example demonstrates that the relative contribution of auto-costimulation to the proliferative responses of costimulator-painted T cells can be augmented by diluting the T cells.

Figure 19:
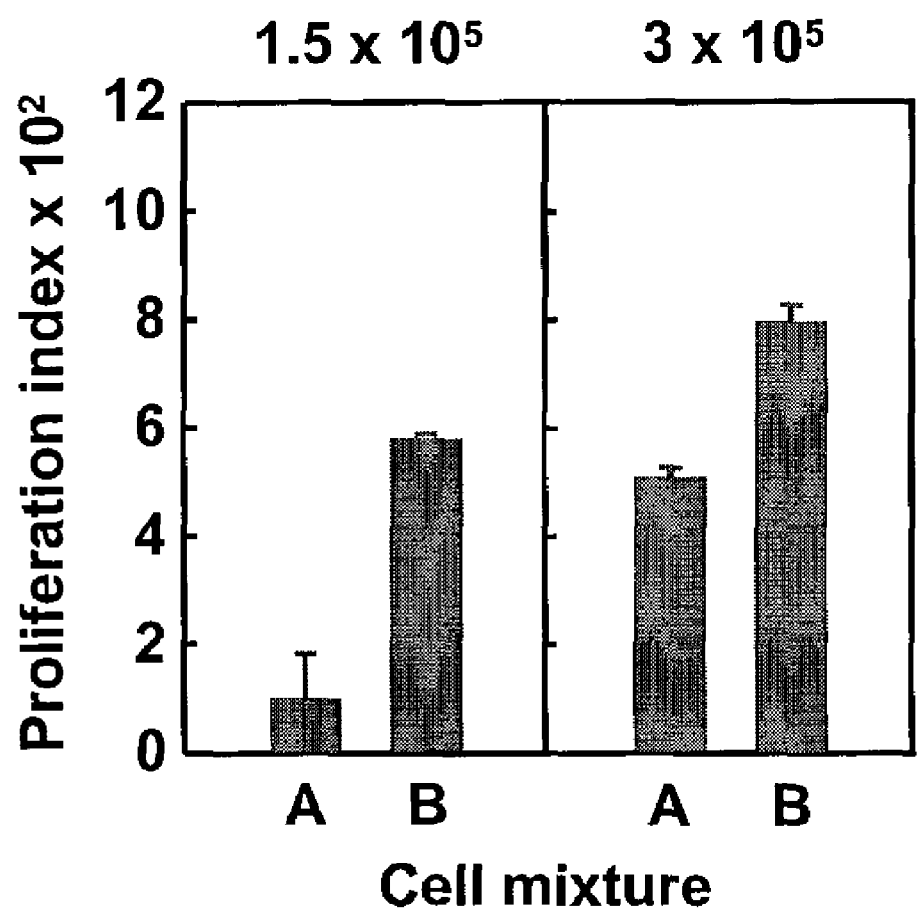
FIG. 19 demonstrates that the relative contribution of cis auto-costimulation, as opposed to intercellular trans costimulation, in a culture of costimulator-painted T cells increases when the cells are diluted, according to the methods of Example 10.

To further validate the auto-costimulation phenomenon, we performed cell dilution analysis. We reasoned that trans intercellular costimulation, which is cell contact-dependent, should decrease disproportionately, as compared to cis auto-costimulation, when one dilutes the cultures. As shown in FIG. 19, this was indeed the case. Specifically, human CD4+ T cells from peripheral blood were used to generate cell mixtures A, B and C, as described above. The mixtures were plated either at $3\times10^5$ cells per well or at half that density, $1.5\times10^5$ cells per well. This two-fold dilution resulted in about a five-fold reduction in the proliferative activity for cell mixture A (trans), in contrast to about a 1.3-fold reduction for cell mixture B (trans+cis). Thus, trans, as opposed to cis, costimulation is preferentially cell-density sensitive. This finding offers yet more evidence that costimulator-painted T cells can signal in both cis- and trans modes, with their relative dominance depending on the experimental setting.

These above examples establish the generality of the auto-costimulated cells of the present invention (different costimulators; cells of different species; cells of different T cell subsets; both primary cells and cell lines), with no undue experimentation required to add to the series of functional auto-costimulated cells in this class. Moreover, the data demonstrate that the protein ligand-painted cells of the present invention auto-stimulate themselves, and do so via painted protein ligands binding to neighboring cognate receptors on the same cell surfaces.

Whereas particular embodiments of this invention have been described above for purposes of illustration, it will be evident to those skilled in the art that numerous variations of the details of the present invention may be made without departing from the invention as defined in the appended claims.

What is claimed is:

1. A method for auto-stimulating a cell comprising: coating the surface of said cell with a first protein, wherein said first protein is a lipidated protein; and
   contacting said cell with a second protein, wherein said second protein is a fusion protein having a first domain having affinity for said lipidated protein and a second domain that binds to a receptor on said cell's surface and engenders a change in the physiological state of said cell, wherein the cell is selected from the group consisting of a T-cell, a tumor-infiltrating lymphocyte, a lymphokine-activated killer cell, a monocyte, a natural killer cell, a neutrophil, an eosinophil, a basophil, a mast cell, a keratinocyte, an endothelial cell, an islet cell, a fibroblast, an osteoblast, a chondrocyte, a muscle cell, a neural cell and a stem cell.

2. The method of claim 1, wherein said T cell is a CD4-positive T cell.

3. The method of claim 1, wherein said T cell is a CD8-positive T cell.

4. The method of claim 1, wherein said T cell is a tumor-infiltrating lymphocyte.

5. The method of claim 1, wherein said T cell has specificity for a tumor antigen.

6. The method of claim 1, wherein said T cell has specificity for a viral peptide antigen.

7. The method of claim 1, wherein said stem cell is selected from the group consisting of a hematopoietic stem cell, a mesenchymal stem cell, and an embryonic stem cell.

8. The method of claim 1, wherein said second domain of said fusion protein comprises a costimulator domain that activates said cell.

9. The method of claim 8, wherein said costimulator domain is selected from the group consisting of B7-1, B7-2, ICAM-1, ICAM-2, ICAM-3, CD48, LFA-3, CD30 ligand, CD40 ligand, heat stable antigen, B7h, 4-1BB ligand, o X40 ligand, LIGHT, CD70 and CD24.

10. The method of claim 1, wherein said second domain of said fusion protein comprises a major histocompatibility complex protein complexed with a peptide antigen.

11. The method of claim 1, wherein said second domain of said fusion protein comprises a domain selected from the group consisting of CD40 ligand, TRANCE, Flt-3 ligand, GM-CSF, VEGF, and FGP.

12. The method of claim 1, wherein said second domain of said fusion protein comprises an inhibitor domain that inhibits said cell.

13. The method of claim 12, wherein said cell is a stem cell.

14. The method of claim 12, wherein said inhibitor domain inhibits or induces apoptosis in a T cell.

15. The method of claim 14, wherein said inhibitor domain is selected from the group consisting of Fas ligand and TRAIL and said cell is a T cell.

16. The method of claim 1, wherein said second domain of said fusion protein comprises a poly-histidine tag.

17. The method of claim 1, wherein said fusion protein comprises a chimeric Fc fusion protein and said lipidated protein is palmitated-protein A.

18. The method of claim 1, wherein said lipidated protein is selected from the group consisting of palmitated-protein A and chelator lipid NTA-DTDA.

19. The method of claim 1, further comprising the step of purifying said cell prior to coating said surface.

20. The method of claim 1, wherein more than one second protein is transferred to said cell.

21. A method for auto-stimulating a cell comprising: coating the surface of said cell with a fusion protein, said fusion protein comprising a first domain and a second domain;
   wherein said first domain becomes incorporated into a membrane of said cell, and said second domain binds to a receptor on said cell's surface and engenders a change in the physiological state of said cell, wherein the cell is selected from the group consisting of a T-cell, a tumor-infiltrating lymphocyte, a lymphokine-activated killer cell, a monocyte, a natural killer cell, a neutrophil, an eosinophil, a basophil, a mast cell, a keratinocyte, an endothelial cell, an islet cell, a fibroblast, an osteoblast, a chondrocyte, a muscle cell, a neural cell and a stem cell.

22. The method of claim 21, wherein said first domain comprises a glycophospholipid.

23. The method of claim 22, wherein said glycophospholipid is glycosyl phosphatidylinositol.

* * * * *